United States Patent
Chang et al.

(10) Patent No.: US 9,254,487 B2
(45) Date of Patent: Feb. 9, 2016

(54) SYSTEMS AND METHODS FOR AN INTEGRATED BIO-ENTITY MANIPULATION AND PROCESSING SEMICONDUCTOR DEVICE

(71) Applicant: Taiwan Semiconductor Manufacturing Company, Ltd., Hsin-Chu (TW)

(72) Inventors: Yi-Hsien Chang, Changhua County (TW); Chun-Ren Cheng, Hsinchu County (TW); Alex Kalnitsky, San Francisco, CA (US); Chun-Wen Cheng, Hsinchu County (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 14/310,440

(22) Filed: Jun. 20, 2014

(65) Prior Publication Data
US 2014/0299472 A1 Oct. 9, 2014

Related U.S. Application Data

(63) Continuation-in-part of application No. 13/716,709, filed on Dec. 17, 2012.

(51) Int. Cl.
*G01N 27/447* (2006.01)
*G01N 27/453* (2006.01)
(Continued)

(52) U.S. Cl.
CPC ..... *B01L 3/502792* (2013.01); *B01L 3/502707* (2013.01); *B81C 1/00523* (2013.01);
(Continued)

(58) Field of Classification Search
CPC .............. H01L 21/02; H01L 21/02107; H01L 21/02104; B01L 2400/0427; B01L 3/502784; B01L 3/502792; G01N 27/447; G01N 27/44704; G01N 27/77791; G01N 27/453
See application file for complete search history.

(56) References Cited

U.S. PATENT DOCUMENTS 6,620,625 B2 * 9/2003 Wolk et al. ............. 436/180
7,189,359 B2 3/2007 Yuan et al.
(Continued)

FOREIGN PATENT DOCUMENTS

TW 201244824 A1 11/2012

OTHER PUBLICATIONS

U.S. Appl. No. 13/716,709, filed Dec. 17, 2012, by inventors Yiu-Hsien Chang and Chun-Ren Cheng for "Systems and Methods for an Integrated Bio-Entity Manipulation and Processing Semiconductor Device," 23 pages of text, 9 pages of drawings.
(Continued)

*Primary Examiner* — Alexander Noguerola
(74) *Attorney, Agent, or Firm* — Haynes and Boone, LLP

(57) ABSTRACT

An integrated semiconductor device for manipulating and processing bio-entity samples is disclosed. The device includes a microfluidic channel that is coupled to fluidic control circuitry, a photosensor array coupled to sensor control circuitry, an optical component aligned with the photosensor array to manipulate a light signal before the light signal reaches the photosensor array, and a microfluidic grid coupled to the microfluidic channel and providing for transport of bio-entity sample droplets by electrowetting. The device further includes logic circuitry coupled to the fluidic control circuitry and the sensor control circuitry, with the fluidic control circuitry, the sensor control circuitry, and the logic circuitry being formed on a first substrate.

20 Claims, 22 Drawing Sheets

(51) Int. Cl.
*B01L 3/00* (2006.01)
*B81C 1/00* (2006.01)
*G01N 33/543* (2006.01)
*H01L 21/02* (2006.01)

(52) U.S. Cl.
CPC ... *G01N33/54366* (2013.01); *B01L 2400/0427* (2013.01); *B81B 2201/0214* (2013.01); *H01L 21/02* (2013.01)

(56) References Cited

U.S. PATENT DOCUMENTS

| | | | |
|---|---|---|---|
| 8,367,370 | B2 | 2/2013 | Wheeler et al. |
| 2004/0231990 | A1* | 11/2004 | Aubry et al. ............... 204/547 |
| 2008/0053205 | A1 | 3/2008 | Pollack et al. |
| 2010/0200781 | A1 | 8/2010 | Khorasani et al. |
| 2010/0236928 | A1 | 9/2010 | Srinivasan et al. |
| 2010/0279374 | A1 | 11/2010 | Sista et al. |
| 2011/0118132 | A1 | 5/2011 | Winger et al. |
| 2013/0293878 | A1 | 11/2013 | Chang et al. |

OTHER PUBLICATIONS

U.S. Appl. No. 14/200,148, filed Mar. 7, 2014, by inventors Kuo-Cheng Ching, Chih-Hao Wang, Zhiqiang Wu, Carlos H. Diaz, and Jean-Pierre Colinge for "Semiconductor Arrangement and Formation Thereof," 17 pages of text, 7 pages of drawings.

Mark A Burns et al., "An Integrated Nanoliter DNA Analysis Device," Science, published by American Association for the Advancement of Science, Oct. 16, 1998, vol. 282, pp. 484-487.

Aaron R. Wheeler, "Putting Electrowetting to Work," Science, published by American Association for the Advancement of Science, Oct. 24, 2008, vol. 322, pp. 539-540.

Mohamed Abdelgawad et al., "The Digital Revolution: A New Paradigm for Microfluidics," 2009 Wiley-VCH Verlag GmbH & Co. KGaA Weinheim, pp. 920-925.

Lin Luan, Randall D. Evans, Nan M. Jokerst, and Richard B. Fair, Integrated Optical Sensor in a Digital Microfluidic Platform, May 2008, pp. 628-635, vol. 8, No. 5, IEEE Sensors Journal.

* cited by examiner

SYSTEMS AND METHODS FOR AN INTEGRATED BIO-ENTITY MANIPULATION AND PROCESSING SEMICONDUCTOR DEVICE

PRIORITY CLAIM AND CROSS-REFERENCE

This is a continuation-in-part of U.S. Ser. No. 13/716,709 filed on Dec. 17, 2012, the entire disclosure of which is hereby incorporated by reference.

The present disclosure is related to the following commonly-assigned patent applications, the entire disclosures of which are incorporated herein by reference: U.S. patent application Ser. No. 13/830,234 filed on Mar. 14, 2013, entitled "OPTICAL DETECTION FOR BIO-ENTITIES", and U.S. patent application Ser. No. 14/200,148 filed on Mar. 7, 2014, entitled "SEMICONDUCTOR ARRANGEMENT AND FORMATION THEREOF".

BACKGROUND

Medical technology industries, including device manufactures as well as pharmaceuticals and biologics manufacturers, have experienced significant commercial and technological growth over the past several decades. Since the discovery of DNA, our understanding of its bio-informational role in the development, operation, and interaction of pathogens and all living beings has significantly increased thanks to the development of DNA sequencing techniques over the years. Through improvement in DNA sequencing detection techniques, scientists and doctors have gained greater insight on diseases as well as more effective treatments for patients based on their genetic dispositions. Thus, the use and role of DNA sequencing results in health care has increased significantly.

DNA sequences are series of the nucleotide bases adenine, guanine, cytosine, and thymine, that dictate the formation of proteins in biological systems. By analyzing a DNA sequence, important information can be gleaned for both diagnostic and therapeutic purposes. Additionally, the identification and quantification of other biological entities (bio-entities), such as proteins, small molecules, and pathogens has pushed forward the potential of medical knowledge to benefit humankind.

There is currently a wide variety of bio-entity manipulation and processing techniques in use today that include the use of amplification and labeling techniques within various methods that may allow for optical detection. This may be done by using fluorescent dyes and external optical systems with analog-to-digital conversion systems to allow for the intensive computer processing required for handling the large amounts of data produced. However, many technical obstacles still exist, such as controlling the fluid samples containing the bio-entity to be observed. Additionally, while the price of DNA sequencing has fallen considerably since the Human Genome Project was completed, further cost savings are needed before the full power of DNA sequencing can have an impact. Therefore, current bio-entity manipulation and processing technologies have not been completely satisfactory.

BRIEF DESCRIPTION OF THE DRAWINGS

Aspects of the present disclosure are best understood from the following detailed description when read with the accompanying figures. It is emphasized that, in accordance with the standard practice in the industry, various features of the figures are not drawn to scale. In fact, the dimensions of the various features may be arbitrarily increased or decreased for clarity of discussion.

Figure 1:
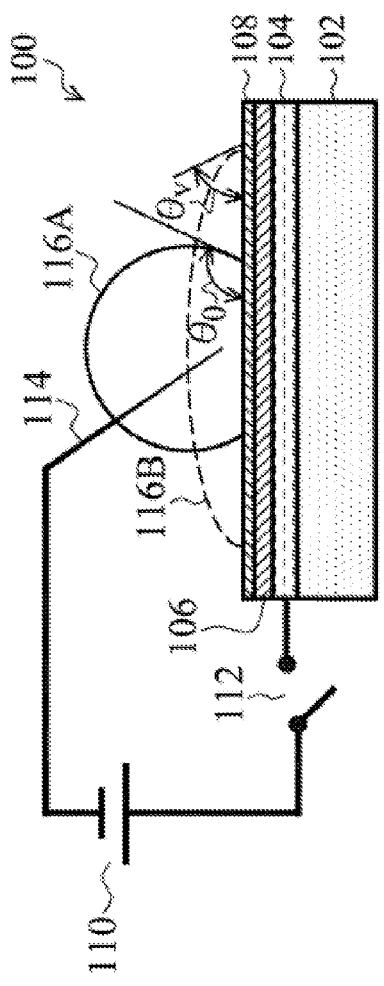
FIG. 1 is a cross-sectional diagram of an electrowetting-on-dielectric apparatus.

The various features disclosed in the drawings briefly described above will become more apparent to one of skill in the art upon reading the detailed description below.

DETAILED DESCRIPTION

It is to be understood that the following disclosure provides many different embodiments and examples for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features in the figures may be arbitrarily drawn in different scales for the sake of simplicity and clarity. Where features depicted in the various figures are common between two or more figures, the same identifying numerals have been used for clarity of description. However, this should not be understood as limiting such features.

FIG. 1 is a cross-sectional diagram of an electro-wetting-on-dielectric (EWOD) apparatus 100. The apparatus 100 includes a substrate 102 with three material layers thereon. These material layers include an electrode layer 104, a dielectric layer 106, and a hydrophobic coating 108. The electrode layer 104 is coupled to a variable voltage source 110 by a switch 112. Attached to the opposite end of the voltage source 110 is a probe 114. As depicted in FIG. 1, the apparatus 100 positions the probe 114 to be inserted into a droplet shown in two different states. Droplet 116A depicts the droplet in a state when no voltage is being applied by probe 114. Because of the hydrophobic coating 108, droplet 116A has a contact angle $\theta_0$ as shown. By applying a voltage from the voltage source 110 through the probe 114, the contact angle can be decreased and the contact area increased. Thus, droplet 116B is the droplet when a voltage is applied. The contact angle is then decreased to $\theta_v$, bringing the mass of the droplet 116B closer to the underlying electrode layer 104. The change in the contact angle caused by the applied voltage is related to the applied voltage according to equation (1) below.

$$\cos\theta_V - \cos\theta_0 = \frac{\varepsilon\varepsilon_o}{2\gamma_{LG}t}V^2 \quad (1)$$

In equation (1), V is the applied electrical potential or voltage, $\theta_V$ is the contact angle under applied voltage V, and $\theta_0$ is the contact angle without applied voltage V. Other variables include: $\varepsilon$, the dielectric constant of the dielectric layer 106; $\varepsilon_0$, the vacuum permittivity; $\gamma_{LG}$, the surface tension; and t, the thickness of dielectric layer 106. This manipulation of the apparent hydrophobicity of the droplet in apparatus 100 may be referred to as electrowetting-on-dielectric (EWOD). Thus, by using EWOD, the physical configuration of a droplet on a hydrophobic surface can be altered and controlled as seen in FIG. 1

Figure 2:
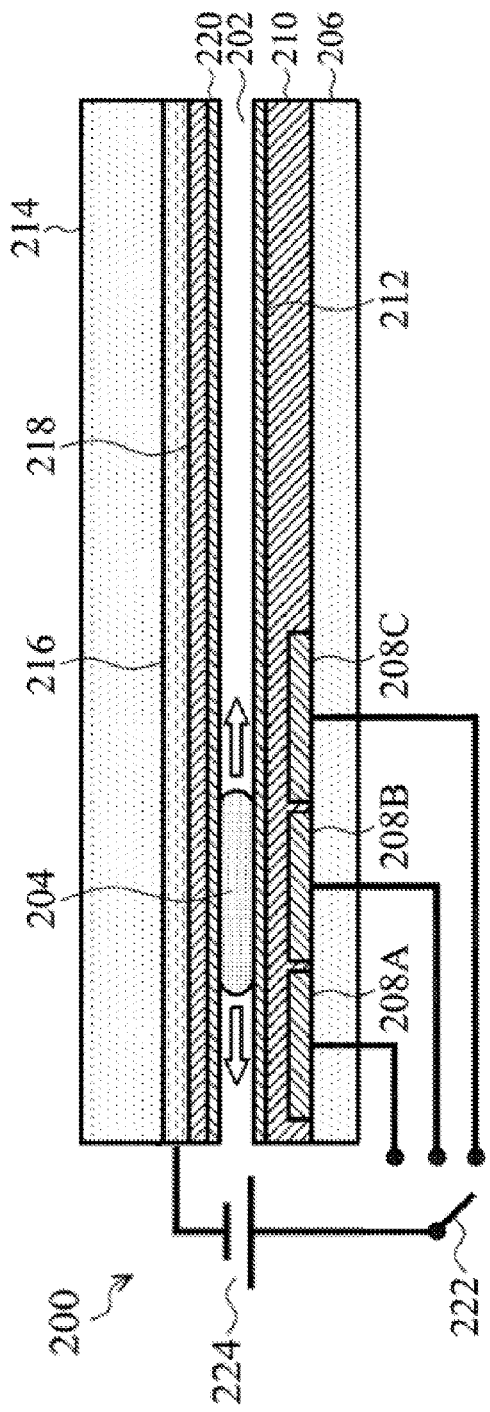
FIG. 2 is a cross-sectional diagram of a fluidic control system that uses electrowetting to transport and manipulate bio-entity sample droplets.

FIG. 2 is a cross-sectional diagram of a fluidic control system 200 that allows for transporting and manipulating bio-entity sample droplets using EWOD principles. The fluidic control system 200 operates around a microfluidic channel 202 to control a droplet 204 within the channel. Droplet 204 is a bio-entity sample droplet. A "bio-entity" or "biological entity" as used herein may refer to DNA, RNA, a protein, a small molecule, a virus or other pathogen, or any such thing that may be sequenced, identified, or quantified. Such activities may take place in a medical or industrial context. Throughout the disclosure, the example of DNA sequencing is presented, however the embodiments are not limited to this example.

As seen in FIG. 2, the bottom portion of the microfluidic channel 202 is provided by a first substrate 206 with several layers thereon. These layers include three electrodes 208A, 208B, and 208C, which are surrounded by a first dielectric layer 210. Above the dielectric layer 210 is a first hydrophobic coating 212 that provides the lower surface of the microfluidic channel 202.

The top surface of the microfluidic channel 202 is provided by another hydrophobic coating, which is formed over a second substrate 214. This second substrate 214 is a glass substrate upon which several material layers are deposited. These layers include a top electrode layer 216, a second dielectric layer 218, and a second hydrophobic coating 220, which forms the top surface of the microfluidic channel 202. The second substrate 214 is inverted and brought close to the surface of the first hydrophobic coating 212. Thus, the droplet 204 is physically bounded by the first hydrophobic coating 212 on the bottom and the second hydrophobic coating 220 on the top.

The bottom electrodes 208A, 208B, and 208C are coupled to a switch 222 capable of selecting any combination of these three electrodes. The switch 222, in turn is connected to a voltage source 224, the opposite side of which is connected to the top electrode layer 216. By selectively applying a voltage to various combinations of electrodes 208A, 208B, and 208C, the electric field in which the droplet 204 is located can be altered. In the depicted embodiment a DC potential is applied, but in other embodiments, an AC potential may be used instead. By controlling the electric fields between the bottom electrodes 208A, 208B, and 208C and the top electrode 216, the droplet 204 itself can be manipulated and transported in various ways. This can be better understood by reference to FIG. 3.

Figure 3:
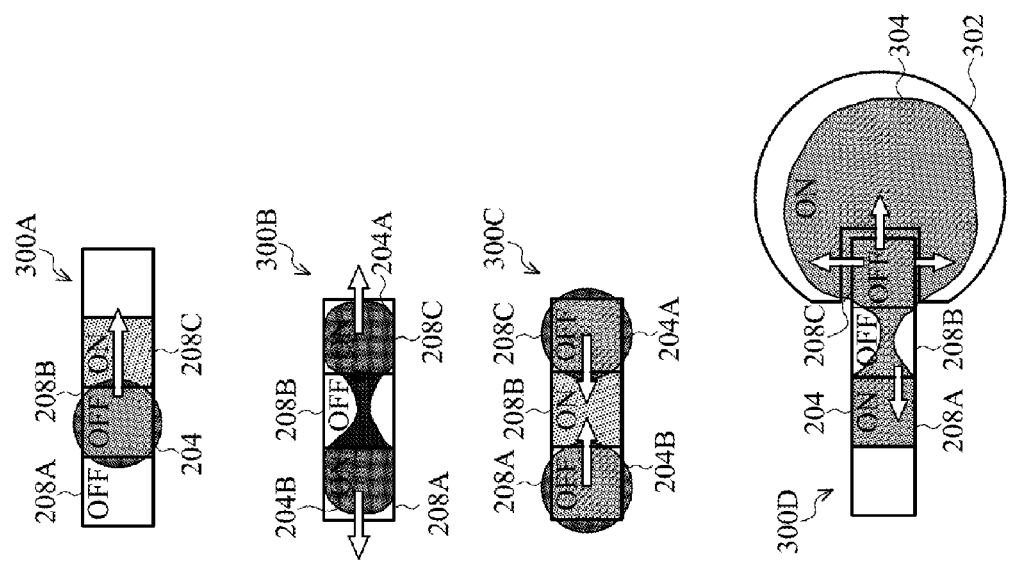
FIG. 3 is a diagram illustrating how certain actions may be achieved using an electrowetting fluidic control system.

FIG. 3 is a diagram illustrating how certain actions may be achieved using an EWOD fluidic control system. Four exemplary actions are depicted: a lateral movement 300A, a droplet split 300B, a droplet merger 300C, and a droplet formation 300D. These examples depict actions performed in the fluidic control system 200 as seen from above, looking down onto the droplet 204 through substrate 214.

As depicted in the lateral movement 300A, the droplet 204 is situated above the electrode 208B. When switch 222 is asserted so that bottom electrode 208A is disconnected from the voltage source 224 (OFF), bottom electrode 208B is OFF, and bottom electrode 208C is connected to the voltage source 224 (ON), the droplet moves in the direction of electrode 208C until it is located over electrode 208C.

As depicted in the droplet split 300B, droplet 204 begins situated above bottom electrode 208B. When switch 222 is asserted so that the bottom electrode 208B is OFF and both bottom electrodes 208A and 208C are ON, the portion of the droplet 204 that is closest to bottom electrode 208A will move to the left and the portion of the droplet 204 that is closest to bottom electrode 208C will move to the right, causing the droplet 204 to be split into a droplet 204A situated over the bottom electrode 208C and a droplet 204B situated over the bottom electrode 208A.

As depicted in the droplet merger 300C, the droplet 204A begins situated above 208C and the droplet 204B begins situated over 208A. When the switch 222 is asserted so that bottom electrodes 208A and 208C are OFF and the bottom electrode 208B is ON, the droplets 204A and 204B both move toward the bottom electrode 208B. The droplets 204A and 204B will merge over the bottom electrode 208B to form a single droplet.

A droplet formation 300D is also depicted in FIG. 3. Droplet formation 300D depicts the formation of a bio-entity sample droplet from a larger bio-entity sample drop. The performance of droplet formation 300D uses the three bottom electrodes 208A, 208B, and 208C, as discussed, and further includes a larger electrode 302. The larger electrode 302 may allow for the placement of a larger volume of liquid in a drop 304. In order to form a droplet 204, all four electrodes (302, 208A, 208B, and 208C) are turned ON to pull the drop 304 out along the path indicated by the square bottom electrodes, then bottom electrodes 208B and 208C are turned OFF. The liquid over bottom electrodes 208B and 208C is pulled away by the ON state of the other electrodes, and pushed away by the hydrophobicity of the bottom electrodes 208B and 208C in their OFF state. The portion of drop 304 above 208A remains to form droplet 204.

These examples assume that any other adjacent electrodes are OFF. The lateral movement 300A, the droplet split 300B, the droplet merger 300C, and the droplet formation 300D actions may be used to manipulate and transport droplets as they move through the microfluidic channel 202 of FIG. 2, and also through a microfluidic grid.

Figure 4:
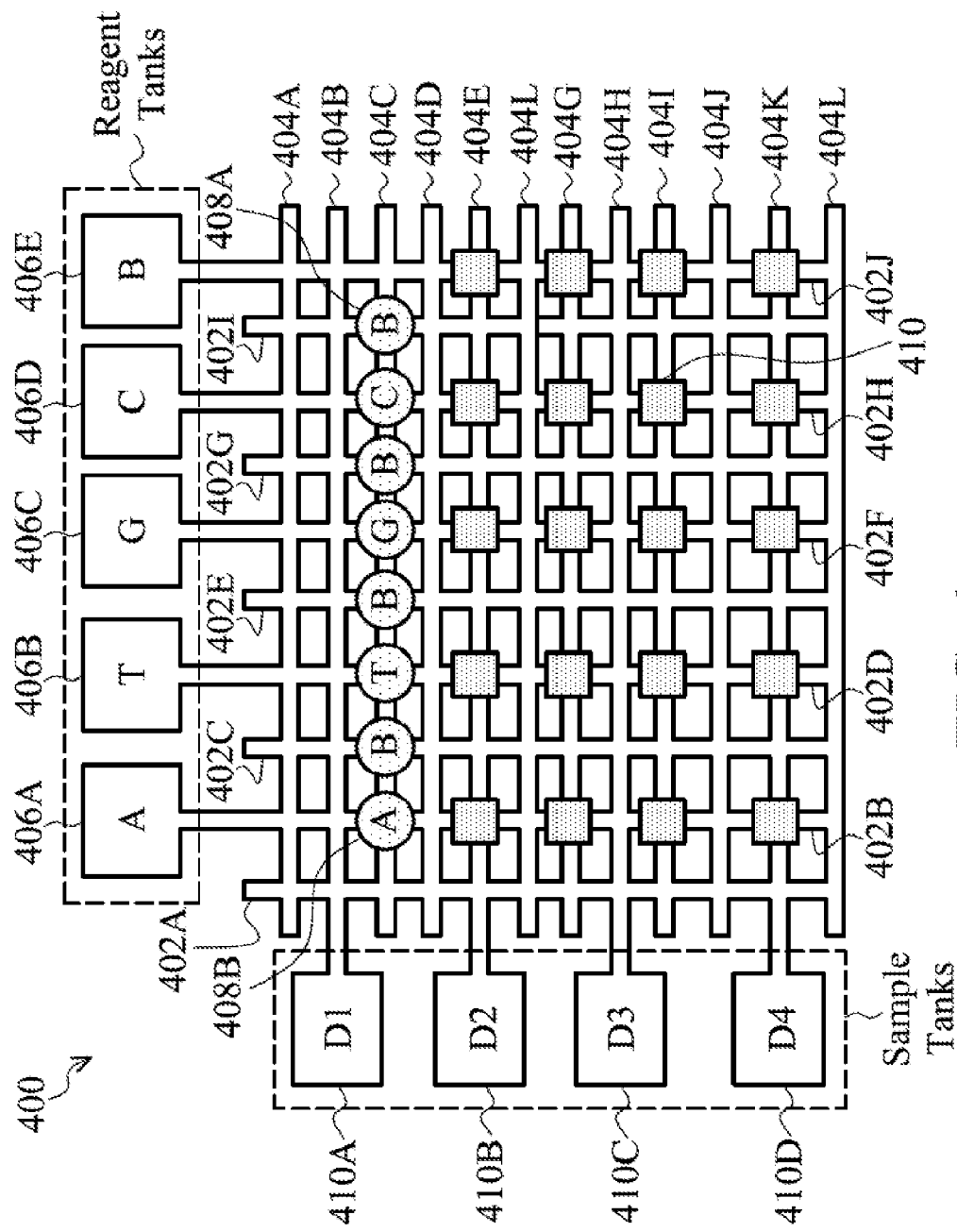
FIG. 4 is a diagram of a microfluidic grid for transporting and mixing target bio-entity samples and biological reagents.

FIG. 4 is a diagram of a microfluidic grid 400 for transporting and mixing target bio-entities. For example microfluidic grid 400 may be used for transporting and mixing target DNA samples and biological reagents. The microfluidic grid includes a plurality of horizontal and vertical paths lined by electrodes like the electrodes 208A, 208B, and 208C of FIG. 2. Actions like those described in connection with FIG. 3 may be used to move, split, merge, and form droplets in the microfluidic grid 400.

The plurality of vertical paths is labeled as vertical paths 402A-J, while the plurality of horizontal paths is labeled as horizontal paths 404A-L. Each of vertical paths 402A-J and each of horizontal paths 404A-L may be formed from a plurality of linearly arranged electrodes. The spaces in between the vertical paths 402A-J and the horizontal paths 404A-L may be empty space as the hydrophobic coatings 212 and 220 may effectively bar a droplet from "jumping" from one hydrophilic path to another with electrodes in an ON state. In some embodiments, material barriers exist in the spaces between the paths.

The microfluidic grid 400 also includes a plurality of tanks from which droplets are introduced into the plurality of paths. Arranged along the top is a number of reagent tanks 406A-E. In the depicted embodiment of microfluidic grid 400, these reagent tanks include an adenine reagent tank 406A, a thymine reagent tank 406B, a guanine reagent tank 406C, a cytosine reagent tank 406D, and a buffer tank 406E. Other embodiments of microfluidic grid 400 may include other biological reagents. Droplets may be dispensed into the microfluidic grid 400 through vertical paths 402B, 402D, 402F, 402H, and 402J, and by selectively asserting the electrodes that make up the horizontal and vertical paths, these droplets may be positioned anywhere in the microfluidic grid 400 and divided and mixed, or merged, with other droplets. A number of reagent droplets, including exemplary buffer droplet 408A and exemplary adenine reagent droplet 408B, are depicted along horizontal path 404C.

Depicted on the left-hand side of microfluidic grid 400 is a number of bio-entity sample tanks 410A-D. In the depicted embodiment, used for DNA sequences, each bio-entity sample tank contains a different target DNA fragment, labeled as D1 in target DNA fragment tank 410A, D2 in target DNA fragment tank 410B, D3 in target DNA fragment tank 410C, and D4 in target DNA fragment tank 410D. In embodiments used for DNA sequencing these tanks hold fragments of a DNA sample to be sequenced. In embodiments used for diagnosis, other types of bio-entity samples, such as antibodies, may be present in the sample tanks.

Sequencing the entire genome of a person or pathogen in a single sequence would require a prohibitively long amount of time. By fragmenting a DNA sample into many samples, each sample may be processed simultaneously in order to decrease the total time required to obtain the entire sequence. The fragments should be labeled beforehand so that the individual parallel sequencing can be recombined. Each square in FIG. 4 is a target DNA fragment, such as exemplary target DNA fragment 410, that can be manipulated as described above in connection with FIG. 3, including being mixed with a reagent droplet for tagging. The area underneath the microfluidic grid 400 includes a light sensor array, which may be used to take light-based measurements in order to sequence the target DNA fragment samples. This may be better understood with reference to FIG. 5.

Figure 5:
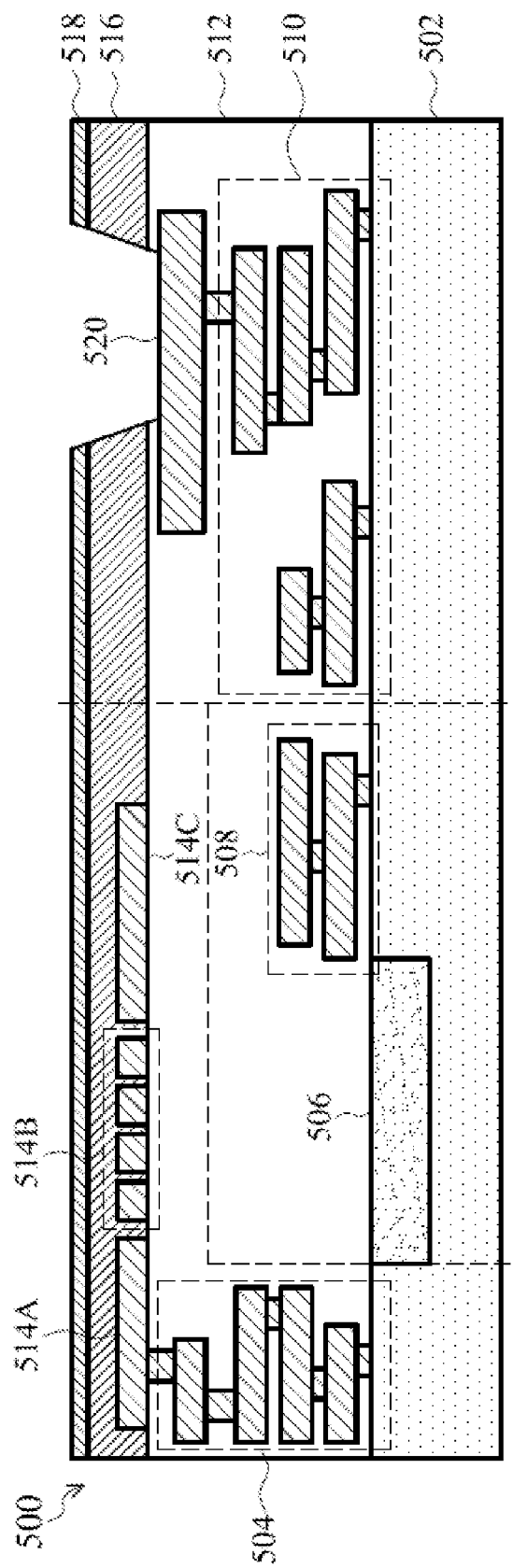
FIG. 5 is a cross-sectional diagram of a lower substrate for use in a bio-entity manipulation and processing system according to an embodiment.

FIG. 5 is a cross-sectional diagram of a lower wafer 500 for use in a microfluidic bio-entity manipulation and processing system. The lower wafer 500 includes four main functional areas: a fluidic control circuitry area, a solid-state based photosensor array area, a logic circuitry area, and a microfluidic channel area. The circuitry and photosensor array areas are formed on or in a substrate 502. As depicted, substrate 502 is a silicon substrate. However, in other embodiments, substrate 502 may be a substrate formed from another suitable elementary semiconductor, such as diamond or germanium; a suitable compound semiconductor, such as silicon carbide, indium arsenide, or indium phosphide; or a suitable alloy semiconductor, such as silicon germanium carbide, gallium arsenic phosphide, or gallium indium phosphide.

The fluidic control circuitry area includes fluidic control circuitry 504, which includes a plurality of metallization layer connected with associated transistors and other circuit components for programming the path of droplet movement. The sensor array area includes a photosensor array 506 and photosensor control circuitry 508. In the depicted embodiment, the photosensor array 506 is an array of transistor-based photosensors and is a CMOS image sensor array. However, in other embodiments the photosensor array may include photodiodes, active pixel sensors, phototransistors, photoresistors, charged coupled devices, or the like. The photosensor array 506 is controlled by the photosensor control circuitry 508, which also includes a plurality of transistors and other circuit components. Finally, in the logic circuitry area, there is a significant amount of logic circuitry 510, including transistors and other circuit components. The logic circuitry 510 allows for input to and output from the lower wafer 500. Further logic circuitry 510 is coupled to both the photosensor control circuitry 508 and the fluidic control circuitry 504, to provide both with signal processing for optimal operation, such as analog-to-digital and digital-to-analog conversion. Fluidic control circuitry 502, photosensor control circuitry 508, and logic circuitry 510 are embedded in an inter-metal dielectric layer (IMD) 512.

On top of the IMD 512, is a plurality of bottom electrodes, much like the bottom electrodes of FIG. 2. Included in FIG. 5, three bottom electrodes are depicted: bottom electrodes 514A, 514B, and 514C. Many more electrodes may be present in practice, but the three depicted are adequate for clear discussion of lower wafer 500. In the depicted embodiment, bottom electrodes 514A, 514B, and 514C are made from an aluminum-copper alloy. However, in other embodiments different materials may be used that are also suitable for electrodes. Bottom electrodes 514A and 514C are solid rectangles as viewed from above, however the bottom electrode 514B is not. This will be discussed further with reference to FIG. 6. In FIG. 5, only the bottom electrode 514A appears to be connected to the fluidic control circuitry metallization stack. However, all bottom electrodes 514A, 514B, and 514C are in communication with the fluidic control circuitry 504, and thus all may be in an ON or OFF state as described in connection with FIG. 3.

On top of and surrounding the sides of bottom electrodes 514A, 514B, and 514C is a dielectric layer 516. In the depicted embodiment, dielectric layer 516 is a high-k dielectric layer formed by an atomic layer deposition (ALD) process, or a chemical vapor deposition (CVD) process, then followed by an annealing process. Over the dielectric layer 516 is a hydrophobic coating 518. In the depicted embodiment, hydrophobic coating 518 is made from polytetrafluoroethylene (PTFE), while in other embodiments it is a self-assembled monolayer. Also depicted in FIG. 5 is a contact pad 520 that is provided by etching through a portion of the hydrophobic coating 518, the dielectric layer 516, and a thickness of IMD 512. Other embodiments may feature additional metal layers and other variations, but in any embodiment, contact pad 520 may be provided to allow power or ground to be supplied to the lower wafer 500, or to allow for signal/control input or output.

Figure 6:
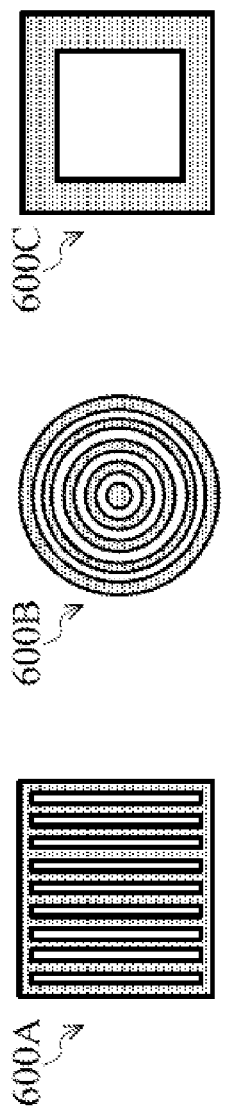
FIG. 6 provides top views of three optical components that may be used in a bio-entity manipulation and processing system according to an embodiment.

FIG. 6 provides top views of three variations of bottom electrode 514B that also serve as optical components that may be used in a bio-entity manipulation and processing system. Thus, in the depicted embodiments, optical components 600A, 600B, and 600C are made from aluminum. Other embodiments may be made from other materials. Optical component 600A is a rectangular grating, including a plurality of regular holes through a rectangular plate. By controlling the proximity and dimensions of the rectangular holes, optical component 600A may separate certain wavelength of light. This may aid in DNA sequencing because some tags generate light at a specific, identifiable frequency when removed. Background noise may be decreased by use of optical component 600A as bottom electrode 514B.

Optical component 600B is a plurality of concentric rings, with regular spacing in between each ring. Using the optical component 600B or other similar component as the bottom electrode 514B may allow for the concentration of light onto the sensor array. Additionally, optical component 600C may be used as the bottom electrode 514B. Optical component 600C may be a pass-through structure that simply allows light to pass through naturally from above the lower wafer 500 down onto the photosensor array 506. Optical component 600C may serve to limit off-axis light from being detected by the photosensor array 506. Other optical components may be used as desired in order to provide optical interference, diffraction, grating, and spectrophotometric functions for bio-optical applications. Optical components 600A, 600B, and 600C are but a few examples. Other embodiments may include a transparent conductor, such as an indium tin oxide (ITO), as the bottom electrode 514B.

Figure 7:
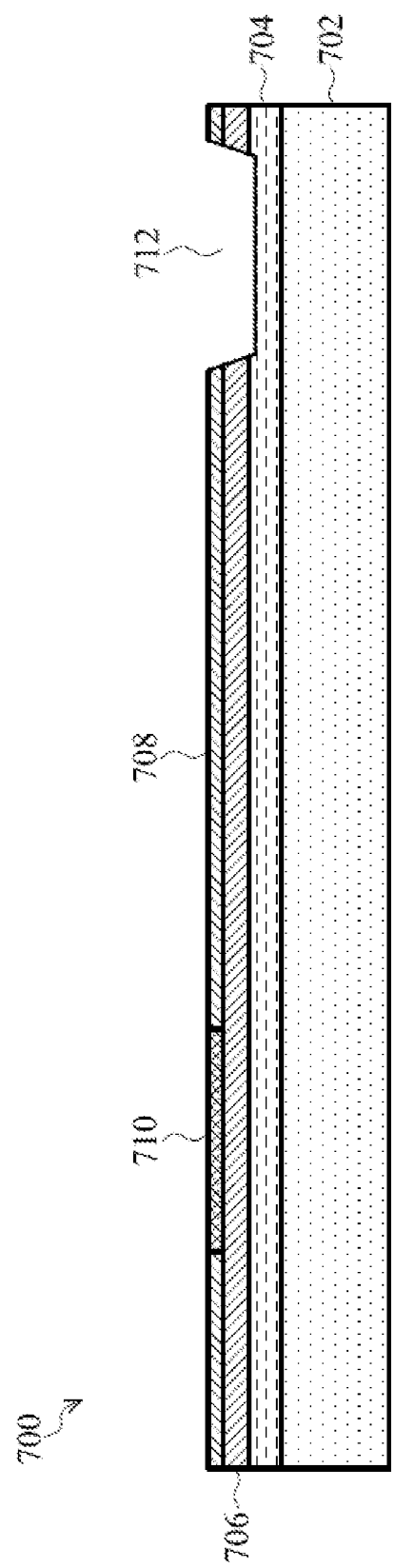
FIG. 7 is a cross-sectional diagram of an upper substrate that may be used in a bio-entity manipulation and processing system according to an embodiment.

FIG. 7 is a cross-sectional diagram of an upper wafer 700 that may be used in a bio-entity manipulation and processing system. The upper wafer 700 includes a substrate 702. In the depicted embodiment, substrate 702 is a glass wafer. However, in other embodiments, substrate 702 may be one of the materials mentioned above in alternate embodiments of substrate 502 of lower wafer 500 in FIG. 5. Over substrate 702 is a top electrode 704. In the depicted embodiment, top electrode 704 is an ITO layer. However, in other embodiments, top electrode 704 may be an aluminum layer or another suitable electrode layer.

A dielectric layer 706 is deposited over the top electrode 704. In this example, the dielectric layer 706 is a high-k dielectric layer that has been deposited by an ALD process before being annealed. Additionally, on top of the dielectric layer 706 is a hydrophobic coating 708. In the depicted embodiment, the hydrophobic coating 708 is made from PTFE, but in other embodiments the hydrophobic coating 708 is made from a self-assembling monolayer. A portion of the hydrophobic coating 708 has been treated with a surface treatment for labeling target DNA fragments, to create a surface treated area 710. In the depicted embodiment, the surface treated area 710 may promote DNA binding, while in other embodiments, an antibody binding surface treatment may be applied. The surface treated area 710 allows identifiable reactions to take place that give of light when a droplet containing components that react with the particular surface treatment are brought into contact with the surface treated area 710. For example, a molecular tag may be added onto base pairs that combine with the target DNA fragment, releasing the tag upon combination, with the release of the tag emitting a light signal.

FIG. 7 also depicts a contact pad area 712. Contact pad area 712 may be formed simply by etching away a portion of the hydrophobic coating 708 and the dielectric layer 706 so that electrical contact may be made with an exposed portion of the top electrode 704. In other embodiments, additional contacting layers may be deposited over the exposed portion of the top electrode 704 to facilitate wire bonding.

Figure 8:
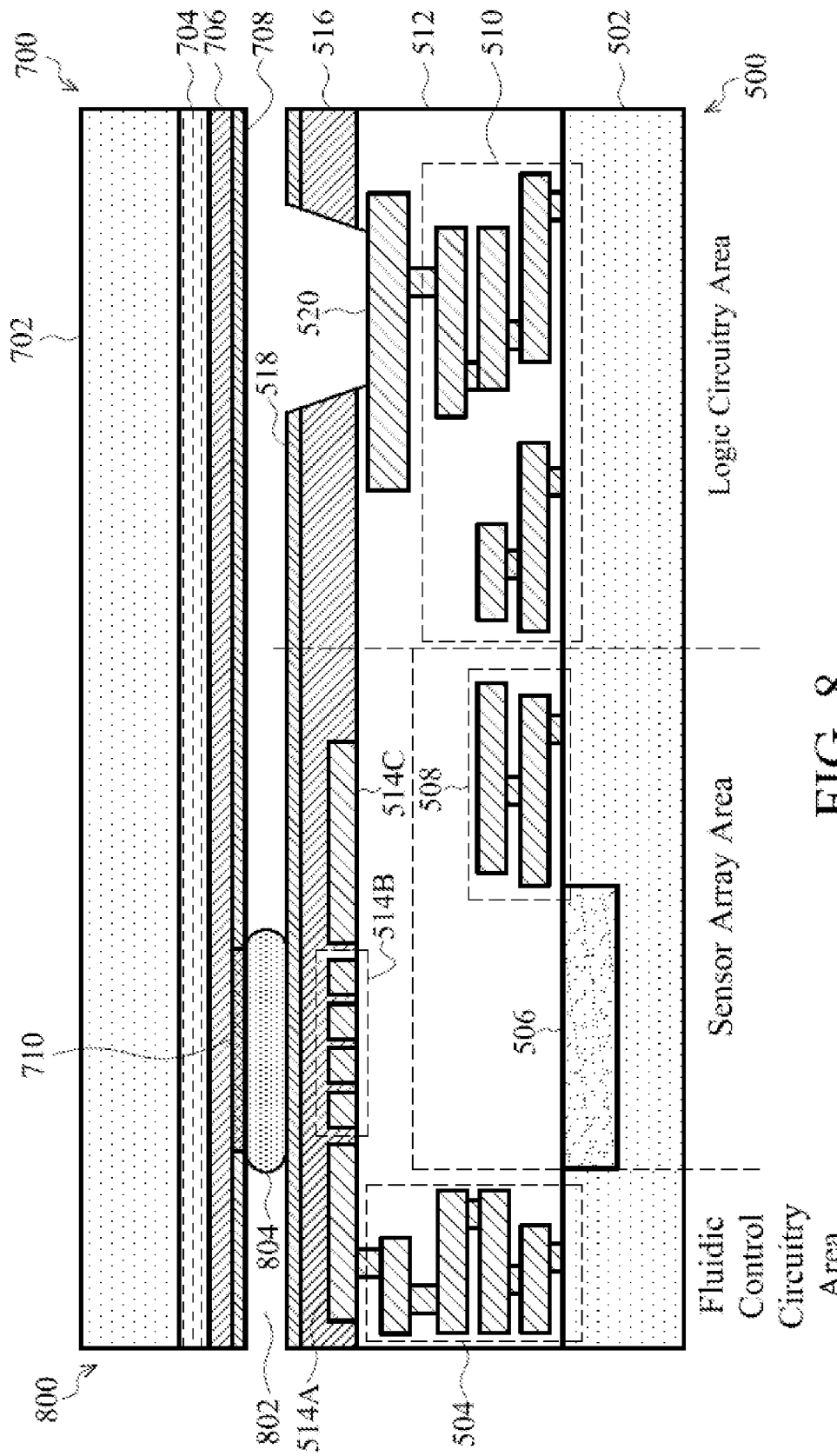
FIG. 8 is a cross-sectional diagram of a microfluidic bio-entity manipulation and processing system according to an embodiment.

FIG. 8 is a cross-sectional diagram of an integrated microfluidic bio-entity manipulation and processing system 800 that integrates the lower wafer 500 of FIG. 5 and the upper wafer 700 of FIG. 7. Thus FIG. 8 includes the substrate 502, with the fluidic control circuitry 504, the photosensor control circuitry 508, and the logic circuitry 510 thereon, in addition to the photosensor array 506 therein. An IMD 512 surrounds those features, and the integrated lower wafer 500 includes bottom electrodes 514A, 514B, and 514C deposited thereon with an overlying dielectric layer 516. On top of the dielectric layer 516 is a hydrophobic coating 518 that serves as the bottom of a microfluidic channel 802.

The microfluidic bio-entity manipulation and processing system 800 also includes substrate 702, which in this embodiment is a glass substrate. Over substrate 702 are a top electrode 704, a dielectric layer 706, and a hydrophobic coating 708. While the depicted embodiment of microfluidic bio-entity manipulation and processing system 700 does not depicted the contact pad area 712 of FIG. 7, other embodiments may contain such a feature. The hydrophobic coating 708 includes a surface treated area 710. The lower wafer 500 and upper wafer 700 are combined using die-level or wafer-level packaging techniques so that the surface treated area 710 is aligned with the photosensor array 506 and so that the hydrophobic coatings 518 and 708 are brought close together, without contacting, to form the microfluidic channel 802. While in the depicted embodiment the surface treated area 710 is formed on hydrophobic coating 708, in other embodiments surface treated area 710 may be formed on hydrophobic coating 518 of lower wafer 500 instead, which may improve performance by bringing the surface treated area 710 closer to photosensor array 506.

In operation, a droplet 804 is brought into contact with the surface treated area 710 using the actions depicted in FIG. 3, such as the lateral movement 300A. The droplet 804 includes a tagged bio-entity sample, such as DNA mixed with a reagent droplet such as the exemplary adenine reagent droplet 408B from FIG. 4. When the droplet 804 contacts the surface treated area 710, chemical reactions may remove the tag from the bio-entity samples in the droplet. The removal of the tag may enhance or intensify a photonic emission. The emission passes through the bottom electrode 514B, which in this embodiment is in the form of the optical component 600A of FIG. 6, and then is sensed in the photosensor array 506. This signal is captured by the photosensor control circuitry 508, and transmitted to the logic circuitry 510 for signal processing. Depending on the frequency or color of the photonic emission, a specific base pair may be detected. In embodiments, in which antibodies in the droplet 804 are being tested, the emission may indicate the presence of the particular antibody in the bio-entity sample in droplet 804. After the droplet 804 has been processed in this manner, it may be moved out of the microfluidic channel 802, and may be moved out of the microfluidic grid 400.

As seen in FIG. 8, the microfluidic bio-entity manipulation and processing system 800 provides microfluidic control circuitry 504 (with associated bottom electrodes 514A, 514B, and 514C), logic circuitry 510, and photosensor array 506, and photosensor control circuitry 508, on a single wafer, lower wafer 500. The lower wafer 500 also provides for a bottom surface of a microfluidic channel 804. The upper wafer 700, bonded to the lower wafer 500, provides the top surface of the microfluidic channel and the top electrode 704. In the depicted embodiment, with high-k dielectric layers 706 and 516, an electric potential of about 5 volts may be used to move and manipulate droplets like droplet 804, as well as power the various circuitry components for image sensing and processing, all on a single chip package.

Figure 9:
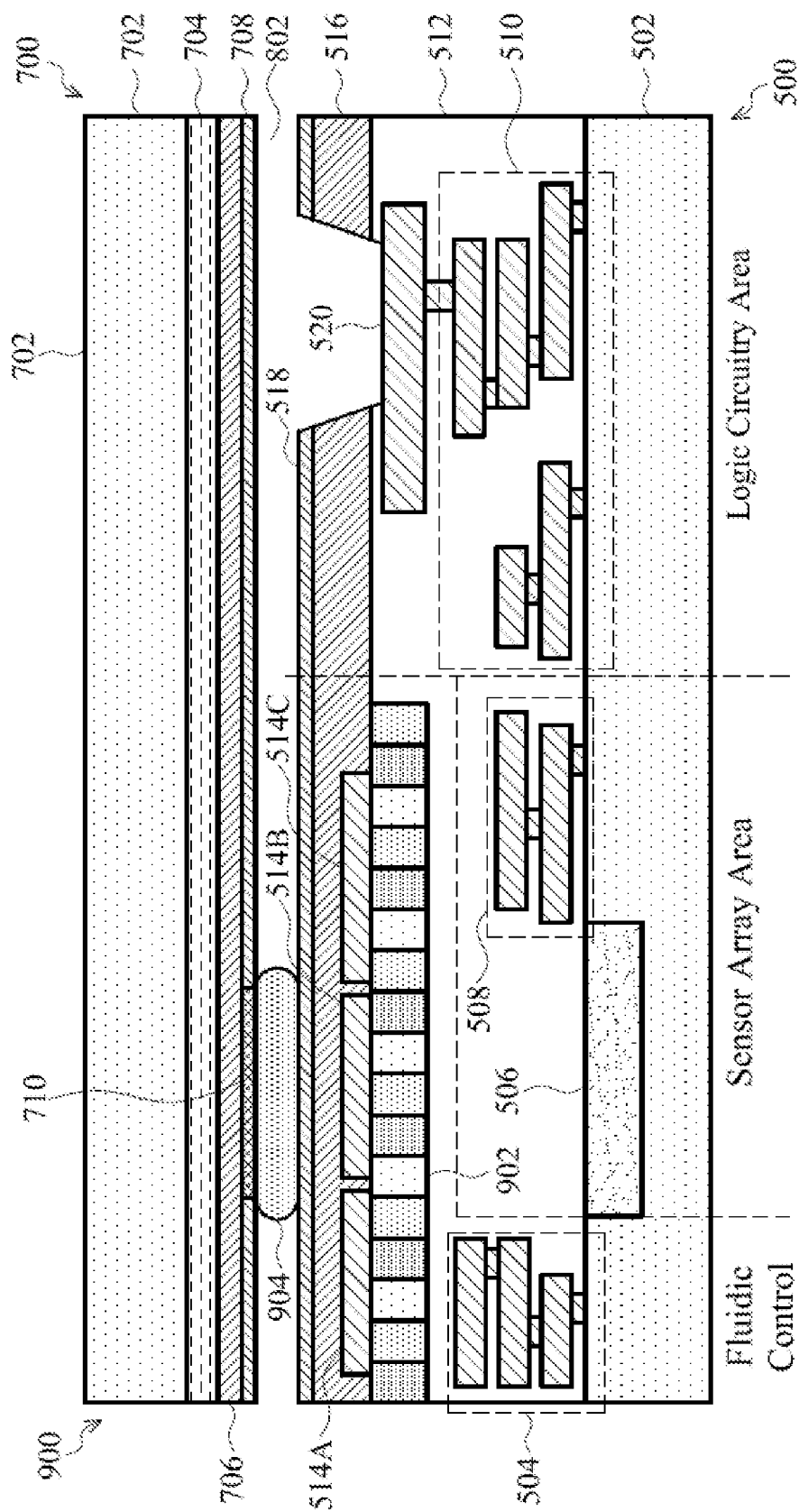
FIG. 9 is a cross-sectional diagram of a microfluidic bio-entity manipulation and processing system according to an additional embodiment that includes a color filter array.

FIG. 9 is a cross-sectional diagram of an integrated microfluidic bio-entity manipulation and processing system 900 according to an additional embodiment that includes a color filter array. Several features are common between the microfluidic bio-entity manipulation and processing system 900 and the microfluidic bio-entity manipulation and processing system 800 of FIG. 8. Such common features are commonly numbered to avoid unnecessary repetition in this disclosure. Underneath the bottom electrodes 514A, 514B, and 514C is a color filter array (CFA) 902, with a plurality of red, blue, and green filters. As depicted in FIG. 9, the bottom electrode 514B is configured as the optical component 600C of FIG. 6. Thus, when an emission is caused by the removal of tag from a bio-entity sample droplet 904 by a reaction at the surface treated area 710, the path passes through the opening of the bottom electrode 514B, through the CFA 902 before entering the photosensor array 506 where the emission can be detected. The addition of the CFA 902 may allow for the more traditional methods of detecting the color of emissions. By detecting the color of the emissions, the particular tag being removed by the reaction at the surface treated area 710 can be identified. In this manner, DNA fragments may be sequenced and specific pathogens may be detected.

While in the depicted embodiment the surface treated area 710 is formed on hydrophobic coating 708 of upper wafer 700, in other embodiments surface treated area 710 may be formed on hydrophobic coating 518 of lower wafer 500 instead, which may improve performance by bringing the surface treated area 710 closer to photosensor array 506.

Figure 10:
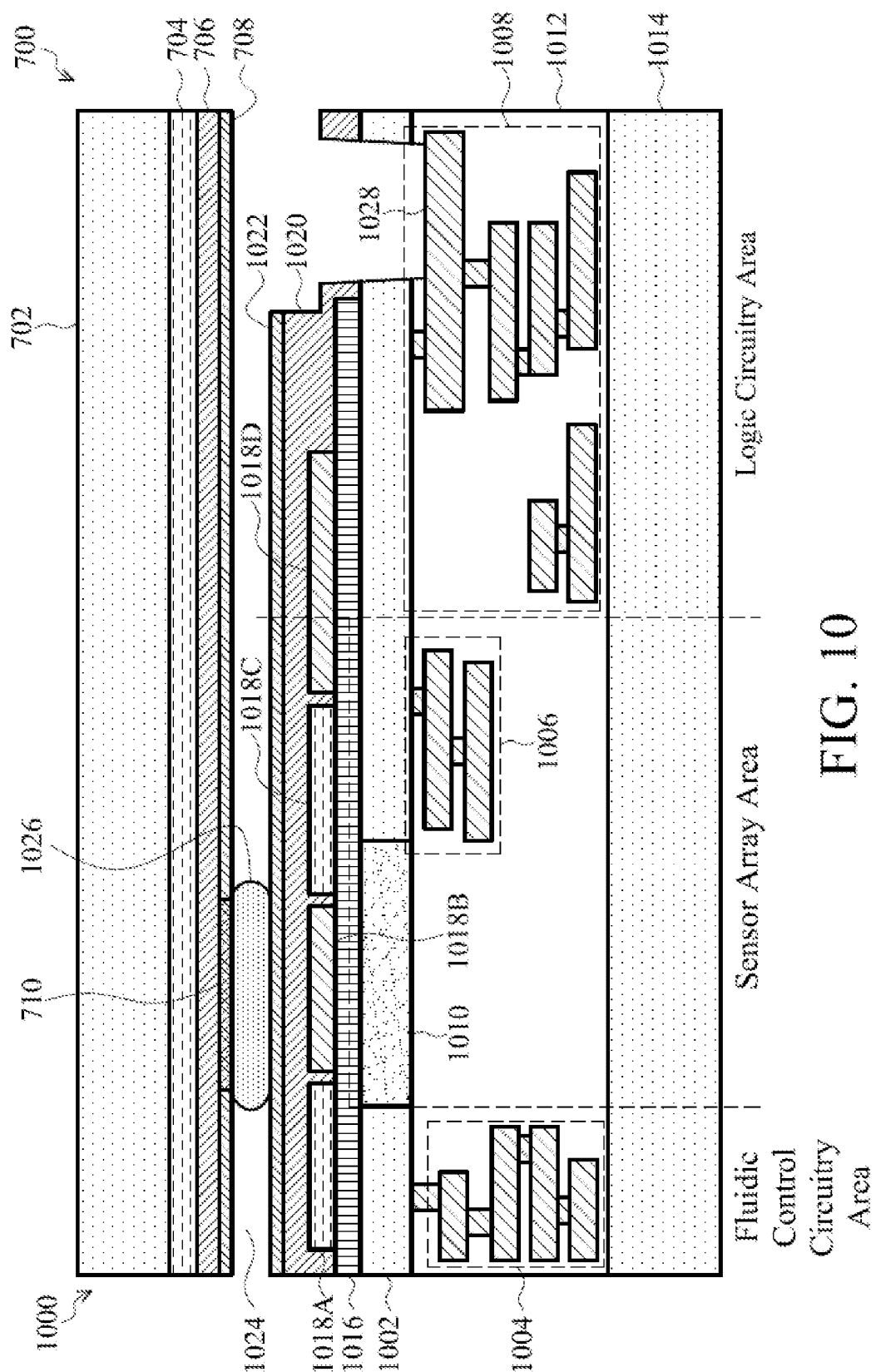
FIG. 10 is a cross-sectional diagram of a lower substrate of a microfluidic bio-entity manipulation and processing system according to an embodiment that utilizes back-side exposure.

FIG. 10 is a cross-sectional diagram of an integrated microfluidic bio-entity manipulation and processing system 1000 according to an additional embodiment that utilizes back-side illumination. The lower wafer of system 1000 is fabricated on a substrate 1002. In the depicted embodiment, substrate 1002 is a P-type silicon substrate, but in other embodiments it may be other materials as described above. During fabrication, a plurality of metal layers is deposited to form fluidic control circuitry 1004, photosensor control circuitry 1006, and logic circuitry 1008. A plurality of photodetectors are fabricated in substrate 1002 to create a photosensor array 1010 that is in communication with photosensor control circuitry 1006. After an IMD 1012 has covered the control and logic circuitries, the material stack on substrate 1002 is bonded to a carrier wafer 1014. Carrier wafer 1014 is a silicon wafer in the depicted embodiment, but may be a glass or other material wafer in other embodiments.

After bonding the carrier wafer 1014 to the top of IMD 1012, the bonded wafers are flipped, and the back side of the substrate 1002 is thinned. In the present embodiment, a high selectivity wet etching process using hydrofluoric, nitric, and acetic acids (HNA) is used to thin substrate 1002. In an alternative embodiment, a chemical mechanical planarization (CMP) process may be used to thin substrate 1002. After the thinning process the photodetectors in the photosensor array 1010 are close to the back side surface of substrate 1002. This may decrease the overall stack height between the photosensor array 1010 and the source of emissions, thereby improving performance.

An anti-reflective coating (ARC) 1016 is deposited and patterned on top of the back side of substrate 1002. In the depicted embodiment, ARC 1016 may be a silicon oxide ARC layer. After the ARC 1016 is patterned a plurality of bottom electrodes may be deposited. FIG. 1000 depicts four bottom electrodes: bottom electrodes 1018A, 1018B, 1018C, and 1018D. In the depicted embodiment, bottom electrodes 1018A and 1018C are transparent bottom electrodes, made from ITO. Meanwhile, bottom electrode 1018B and 1018D are back side metal electrodes made of an aluminum-copper alloy. Other configurations and materials may be used for the bottom electrodes 1018A, 1018B, 1018C, and 1018D in other embodiments. In embodiments where more than one material is used for the bottom electrodes, different processes will be used for deposition and patterning. In general, a portion of the photosensor array 1010 is covered by an opaque material, which in the depicted embodiment is provided by bottom electrode 1018B. This opaque material is used as a dark reference, to determine the amount of signal from the photosensor 1010 that is attributable to sources other than visible light, such as heat.

A dielectric layer 1020 is deposited on top of the bottom electrodes, as well as the exposed portions of ARC 1016 and the back side of substrate 1002. In the depicted embodiment, the dielectric layer 1020 is a high-k dielectric layer, deposited by an ALD process and then annealed, while in other embodiments dielectric layer 1020 is deposited by a CVD before annealing. Over the dielectric layer 1020, a hydrophobic coating 1022 is deposited. Hydrophobic coating 1022 provides the bottom half of a microfluidic channel 1024, through which a droplet 1026 may be moved. In the depicted embodiment, the hydrophobic coating 1022 is made from PTFE. In other embodiments, it may be a self-assembling monolayer. Also depicted in FIG. 10 is a contact pad 1028 formed by etching through the hydrophobic coating 1022, the dielectric layer 1020, through substrate 1002 and a portion of IMD 1012. Contact pad 1028 provides a location for wire bonding to allow for input and output as well as a power supply connection to logic circuitry 1008 and other circuitry embedded in IMD 1012.

The wafer based on lower substrate 1002 is bonded to an upper wafer, like upper wafer 700 of FIG. 7. Thus, the upper wafer 700 includes a substrate 702, a top electrode 704, a dielectric layer 706, and a hydrophobic coating 708 with a surface treated area 710. Along with the hydrophobic coating 1022, hydrophobic coating 708 forms the microfluidic channel 1024. As discussed with other embodiments herein, the droplet 1026 can be moved into contact with the surface treated area 710, which provides a site for characteristic biochemical interactions with bio-entities that emit light. These light emissions are detected by the photosensor array 1010 and then processed to determine the entities involved in the reaction. By determining these entities, a nucleotide base or a specific antibody may be registered. While in the depicted embodiment the surface treated area 710 is formed on hydrophobic coating 708, in other embodiments surface treated area 710 may be formed on hydrophobic coating 1022 of the wafer based on lower substrate 1002 instead, which may improve performance by bringing the surface treated area 710 closer to photosensor array 1010.

Figure 11:
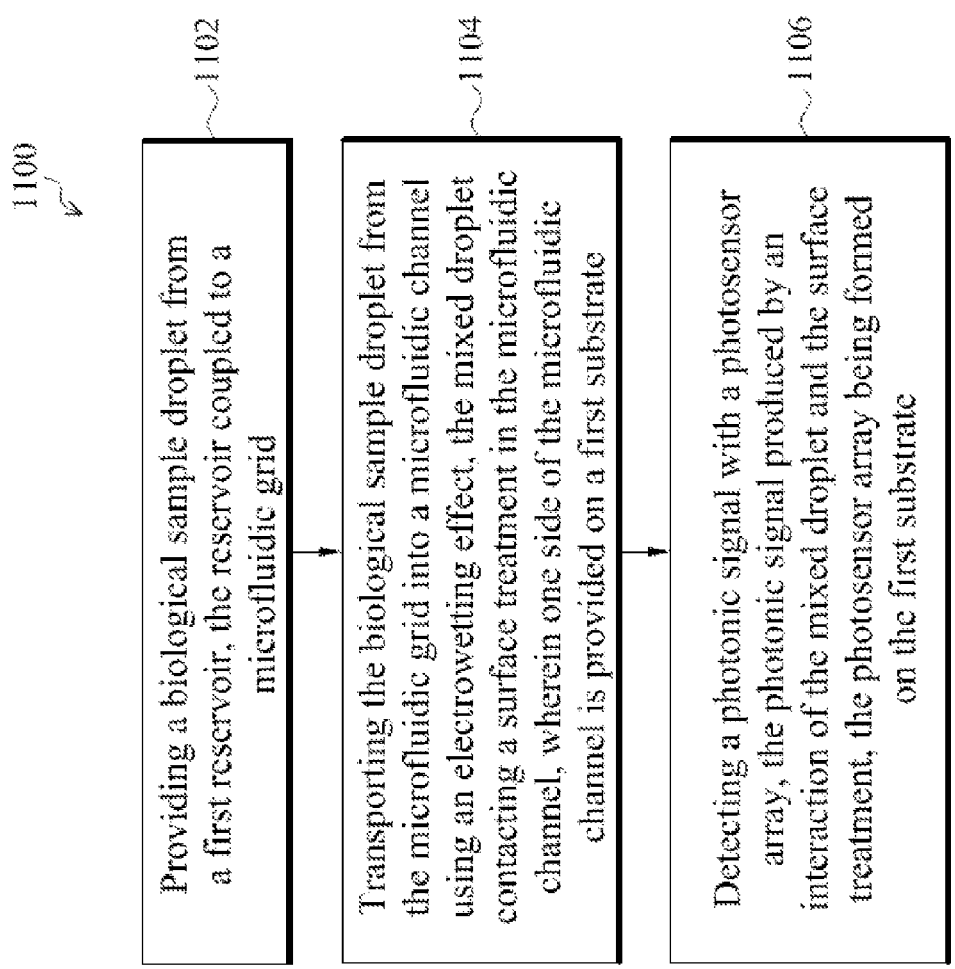
FIG. 11 is a flowchart of a method for manipulating and processing bio-entity samples with an integrated semiconductor device.

FIG. 11 is a flowchart of a method 1100 for manipulating and processing bio-entity samples with an integrated semiconductor device. The method 1100 begins in step 1102 when a bio-entity sample droplet is obtained from a first reservoir. The first reservoir is coupled to a microfluidic grid. The method 1100 may continue in step 1104 when the bio-entity sample droplet is transported from the microfluidic grid into a microfluidic channel using an electrowetting effect. The microfluidic channel has a side provided on a first substrate. When in the microfluidic channel the bio-entity sample droplet contacts a surface treatment in the microfluidic channel. A biochemical reaction is triggered upon contact between the bio-entity sample droplet and the surface treatment. In step 1106, a photonic signal that is produced by the interaction of the bio-entity sample droplet and the surface treatment is detected by a photosensor array that is formed on the first substrate.

To better illustrate method 1100 in operation, reference will be made to the integrated microfluidic bio-entity manipulation and processing system 800 of FIG. 8 and some other figures discussed above such as FIG. 3 and FIG. 4. Method 1100 may also be explained with reference to other embodiments of integrated microfluidic bio-entity manipulation and processing systems disclosed herein. Thus, reference to FIG. 8 is made by way of non-limiting example. A reservoir 410A of FIG. 4 may include a larger volume of a bio-entity sample. By using the action depicted as droplet formation 300D of FIG. 3, a bio-entity sample droplet 804 is formed from the larger volume and introduced into the microfluidic grid 400 of FIG. 4 (step 1102). The bio-entity sample droplet 804 is transported through microfluidic grid 400, which includes a plurality of microfluidic channels, one of which is microfluidic channel 802 of FIG. 8. Microfluidic channel 802 is located on top of a material stack deposited on substrate 502, the top layer of which, hydrophobic coating 518, supplies the bottom surface of the microfluidic channel 802. Transporting the bio-entity sample droplet 804 through the microfluidic channel is accomplished by using the logic circuitry 510 to control the fluidic control circuitry 504.

The bio-entity sample droplet 804 is moved through the microfluidic grid 400 of FIG. 4 and the microfluidic channel 802 of FIG. 8 by using the electrowetting effect. Bottom electrodes 514A, 514B, and 514C are asserted in either ON or OFF states as indicated by FIG. 3, in order to subject the biological droplet to controlled hydrophobic or hydrophilic surfaces according to the ON or OFF states of the bottom electrodes. By control of the bottom electrodes 514A, 514B, and 514C, and in conjunction with a top electrode 704, the bio-entity sample droplet 804 is guided into contact with the surface treated area 710, which has had a surface treatment applied to it (step 1104). Guiding the bio-entity sample droplet 804 into contact with the surface treated area 710 is accomplished by having the logic circuitry 510 exert control over the fluidic control circuitry 504.

Because of the surface treatment, surface treated area 710 and the bio-entity sample droplet 804 may undergo a biochemical reaction which intensifies or enhances the fluorescent light signal. This light passes through the bottom electrode 514B to a photosensor array 506. Photosensor 506 detects the light and a corresponding signal is sent to the logic circuitry 510 for processing (step 1106). Logic circuitry 510 may interpret the signal by color or frequency to determine the biochemical reaction that occurred. The biochemical reaction may indicate that a specific base nucleotide was detected in a target DNA fragment, or that a particular antibody was present in the bio-entity sample droplet. After the bio-entity sample droplet 804 has been processed, it may be removed from the microfluidic channel 802. In some embodiments a buffer droplet, such as buffer droplet 408A of FIG. 4, may be transported through the microfluidic channel 802 in order to clean it.

Additionally, in some embodiments of method 1100, an adenine reagent droplet 408B obtained from the adenine reagent tank 406A in FIG. 4 is combined with the bio-entity sample droplet 804, using the droplet merge 300C operation of FIG. 3. The droplet merge 300C operation may mix the bio-entity sample droplet 804 and the adenine reagent droplet 408B in the microfluidic grid 400. The mixed bio-entity sample droplet 804 may then be directed into contact with the surface treated area 710 in the microfluidic channel 802. In some embodiments, bottom electrode 514B may be an optical component in addition to acting as an electrode. Thus the bottom electrode 514B may be optical component 600A in one embodiment, and 600B in another embodiment. In other embodiments, a reagent other than the adenine reagent droplet 408B may be used to create a different mixed bio-entity sample droplet 804.

One of the broader embodiments is an integrated semiconductor device for manipulating and processing bio-entity samples. The device may include a microfluidic channel, the channel being coupled to fluidic control circuitry, and a photosensor array coupled to sensor control circuitry. The device may also include logic circuitry coupled to the fluidic control circuitry and the sensor control circuitry. The fluidic control circuitry, the sensor control circuitry, and the logic circuitry may be formed on a front side of a first substrate.

Another of the broader embodiments is an integrated semiconductor device for manipulating and processing genetic samples. The integrated semiconductor device may include a microfluidic channel, the microfluidic channel being coupled to fluidic control circuitry. The device may further include a photosensor array coupled to sensor control circuitry, an optical component aligned with the photosensor array to manipulate a light signal before the light signal reaches the photosensor array, and a microfluidic grid coupled to the microfluidic channel and providing for transport of genetic sample droplets by electrowetting. Additionally, the device may include logic circuitry coupled to the fluidic control circuitry and the sensor control circuitry. The fluidic control circuitry, the sensor control circuitry, and the logic circuitry are formed on first substrate.

Yet another of the broader embodiments is a method for manipulating and processing bio-entity samples with an integrated semiconductor device. The method may include steps of providing a bio-entity sample droplet from a first reservoir, the first reservoir coupled to a microfluidic grid; transporting the bio-entity sample droplet from the microfluidic grid into a microfluidic channel using an electrowetting effect, and detecting a photonic signal with a photosensor array. The bio-entity sample droplet may contact a surface treatment in the microfluidic channel, wherein one side of the microfluidic channel is provided on a first substrate. The photonic signal is enhanced by an interaction of the bio-entity sample droplet and the surface treatment, and the photosensor array is formed on the first substrate.

Figure 12A:
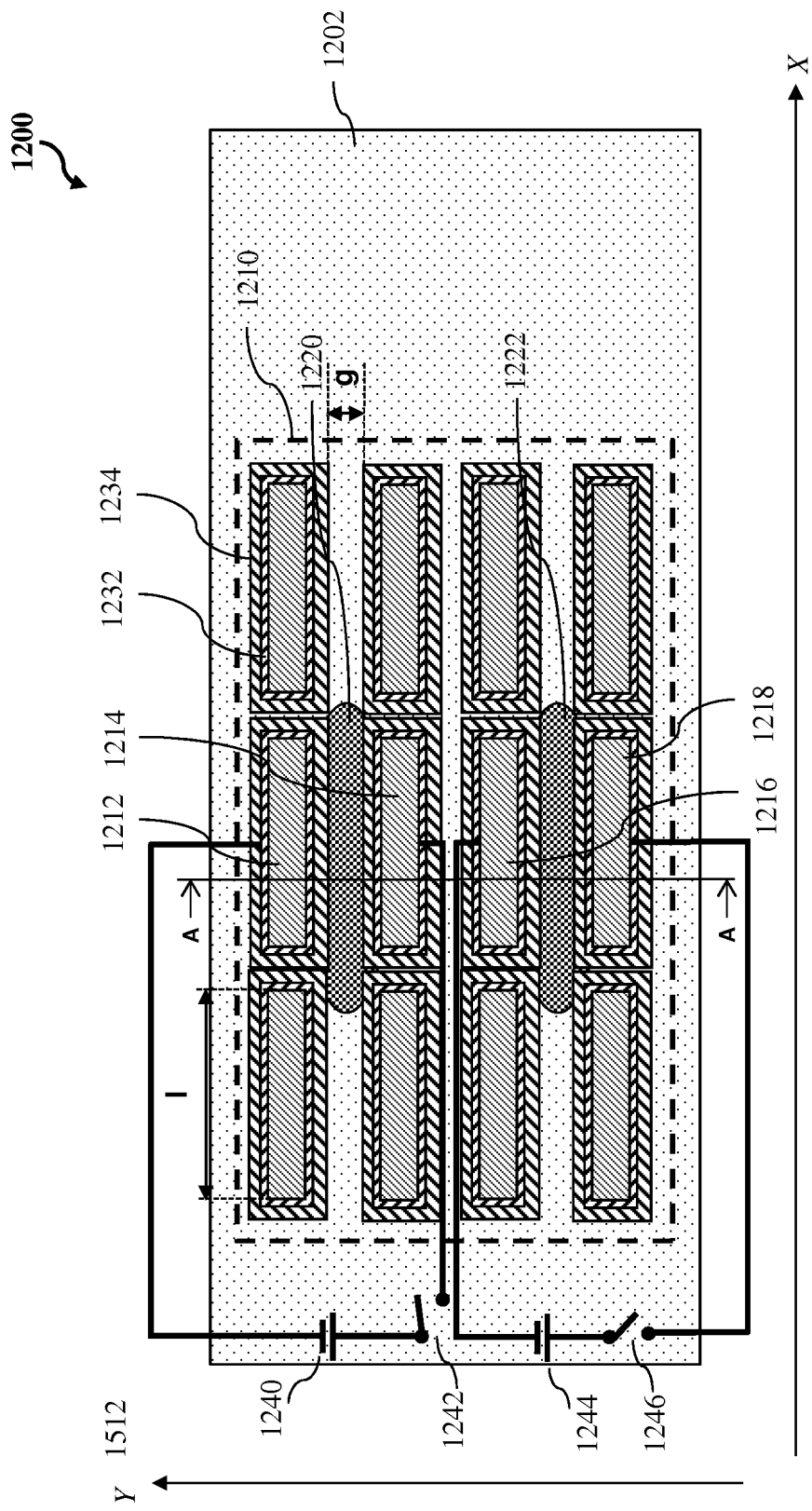
FIG. 12A is a top view illustrating a lower wafer in a microfluidic bio-entity manipulation and processing system according to some embodiments of the present disclosure.

FIG. 12A is a top view illustrating a lower wafer 1200 including one or more vertical electrodes 1210 in a microfluidic bio-entity manipulation and processing system according to some embodiments. In some embodiments, the lower portion 1202 of the lower wafer 1200 may include a substrate, a photosensor array, one or more circuitries embedded in an inter-metal dielectric layer (IMD) as discussed with regard to FIG. 5. In some embodiments, each of the vertical electrodes has a length along X-dimension in a range from about 50 µm to about 5000 µm. As shown in FIG. 12A, a channel gap (g) between the two adjacent vertical electrodes along the Y-dimension is in a range from about 30 µm to about 1000 µm.

Still referring to FIG. 12A, a droplet 1220 is brought into contact with the vertical electrodes 1212 and 1214, and a droplet 1222 is brought into contact with the vertical electrodes 1216 and 1218. The vertical electrode 1212 is coupled to a voltage source 1240, and the voltage source 1240 is coupled to a switch 1242 capable of selecting any status between ON and OFF by connecting or disconnecting the switch 1242 to the vertical electrode 1214. Similarly, the vertical electrode 1216 is coupled to a voltage source 1244, and the voltage source 1244 is coupled to a switch 1246 capable of selecting any status between ON and OFF by connecting or disconnecting the switch 1246 to the vertical electrode 1218. By selectively applying a voltage between vertical electrodes 1214 and 1214, an electric field applied to the droplet 1220 can be altered, manipulated and transported in various ways. Similarly, by selectively applying a voltage to vertical electrodes 1216 and 1218, an electric field applied to the droplet 1222 can be altered, manipulated and transported in various ways. In the depicted embodiment a DC potential is applied, but in other embodiments, an AC potential may be used instead.

Figure 12B:
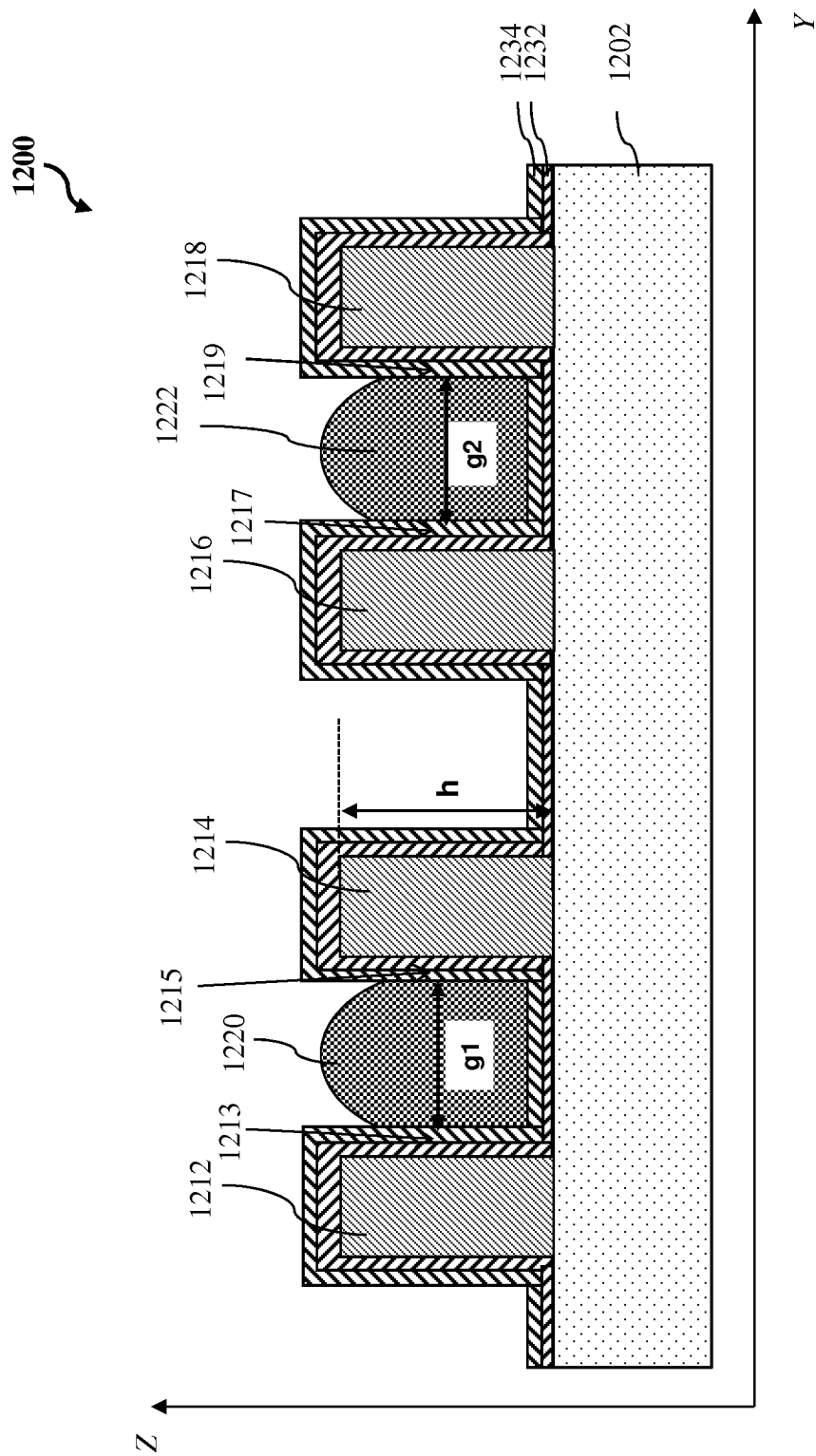
FIG. 12B is a cross-sectional view of the lower wafer in a microfluidic bio-entity manipulation and processing system along the line A-A in FIG. 12A according to some embodiments of the present disclosure.

FIG. 12B is a cross-sectional view of the lower wafer 1200 including the vertical electrodes 1210 along the line A-A in FIG. 12A according to some embodiments. As shown in FIG. 12B, the one or more electrodes on the lower portion 1202 are vertical electrodes 1210, so that the droplets 1220 and 1222 may be moved within the channel gap (g) between two adjacent rows of the vertical electrodes. For example, the droplet 1220 may be moved in a channel gap (g1) between the vertical electrode 1212 and the vertical electrode 1214, and the droplet 1222 may be moved in a channel gap (g2) between the vertical electrode 1216 and the vertical electrode 1218. Each of the vertical electrodes has a height (h) along Z-dimension in a range from about 2 µm to about 100 µm. The droplet 1220 and/or the droplet 1222 may be substantially similar to the droplet 804, which may include a tagged bio-entity sample.

In some embodiments, a dielectric layer 1232 may be formed on and conformed to the surface of each of the vertical electrodes 1210. The dielectric layer 1232 may include a high-k dielectric material, and may be deposited using an ALD process or a CVD process followed by an annealing process. A hydrophobic coating 1234 may be further formed on the dielectric layer 1232, and the hydrophobic coating 1234 may also be conformed to the surface of each of the vertical electrodes 1210. Referring back to FIG. 12A, in some embodiments, the dielectric layer 1232 and/or the hydrophobic coating 1234 formed on the adjacent vertical electrodes may offer sufficient isolation between the two adjacent vertical electrodes along the X dimension; meanwhile, the dielectric layer 1232 and/or the hydrophobic coating 1234 formed on the adjacent vertical electrodes may also prevent the droplets from diffusing into the space between the vertical electrodes along the X-dimension.

Figure 12C:
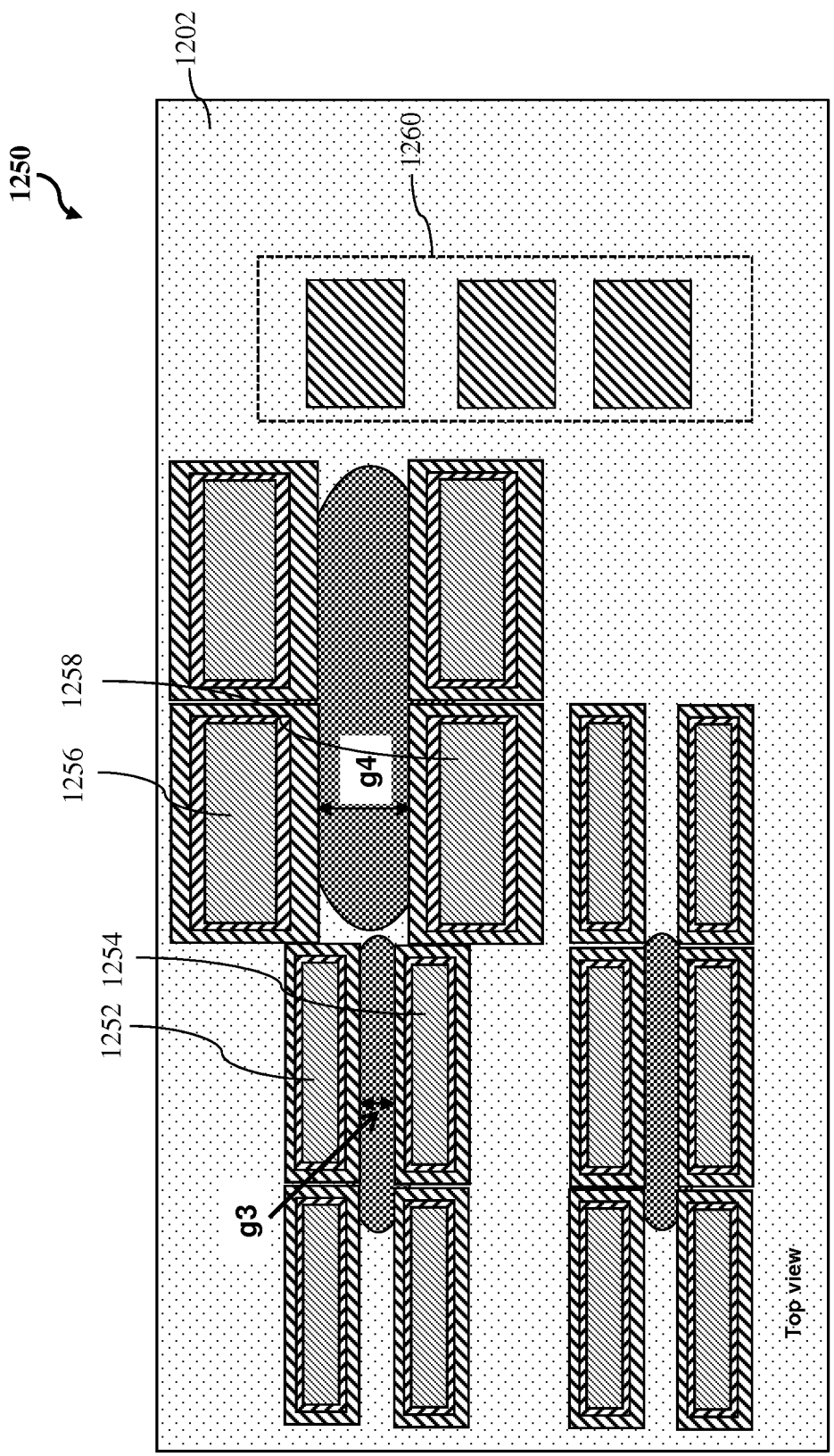
FIG. 12C is a top view illustrating a lower wafer in a microfluidic bio-entity manipulation and processing system according to some embodiments of the present disclosure.

FIG. 12C is a top view illustrating a lower wafer 1250 in a microfluidic bio-entity manipulation and processing system according to some embodiments of the present disclosure. The layout of the one or more vertical electrodes on the lower wafer 1250 may be designed to offer different channels gaps for holding different droplet volumes. For example, the channel gap between the vertical electrode 1256 and the vertical electrode 1258 may be substantially greater than the channel gap (g3) between the vertical electrode 1252 and the vertical electrode 1254. Therefore, the channel gap (g4) is able to hold a droplet 2 with greater volume than a droplet 1 being held by the channel gap (g3). The various embodiments of the vertical electrode design layout may offer more flexibility for testing the samples with different volumes using the microfluidic bio-entity manipulation and processing system as discussed in the present disclosure. The lower wafer 125 may also include one or more contact pads 1260 for supplying power or ground to the lower wafer 1250, or for providing signal/control input or output.

Figure 13A:
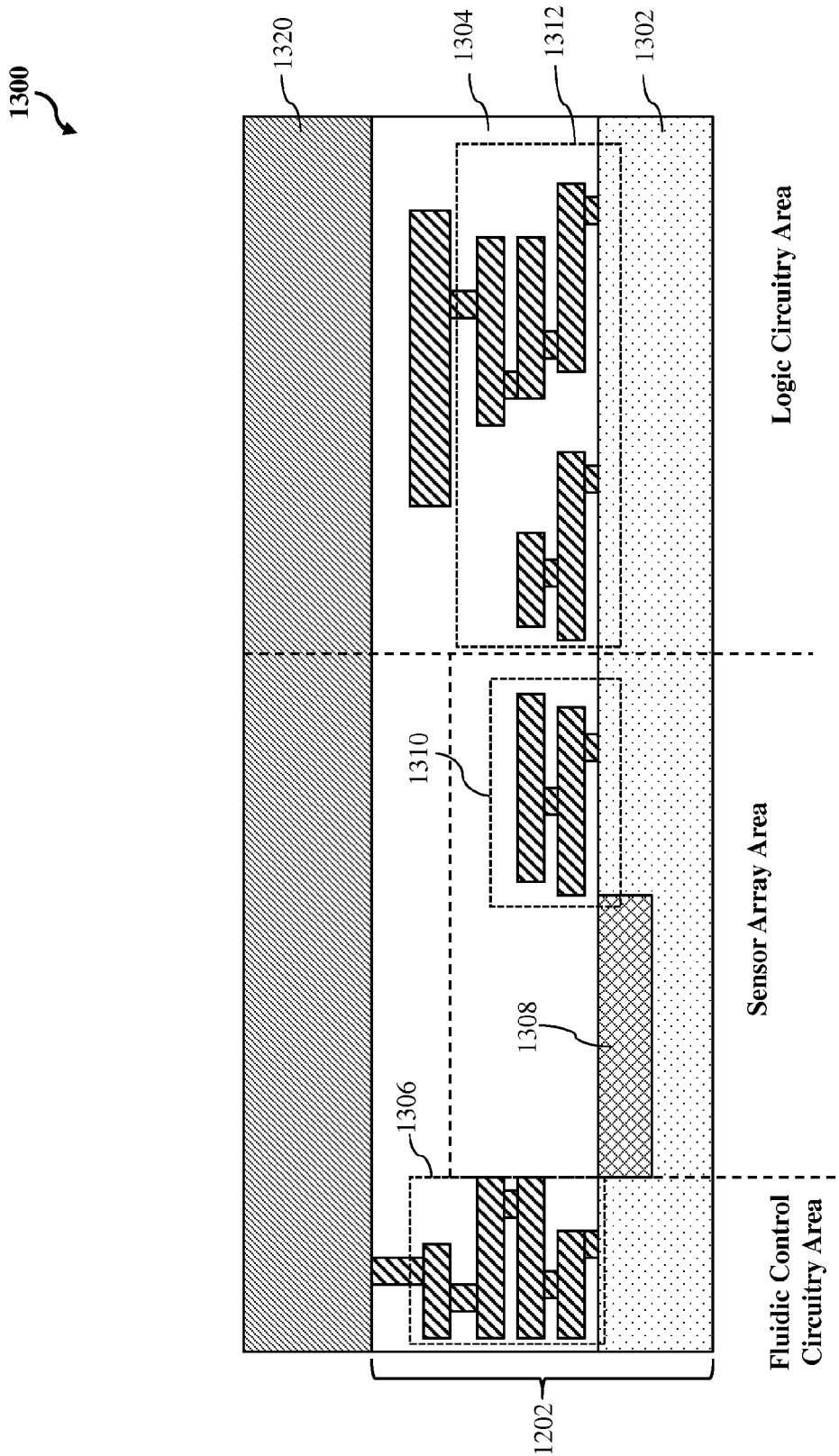
FIGS. 13A-13E are cross-sectional views of a lower wafer in a microfluidic bio-entity manipulation and processing system fabricated at various steps according to some embodiments of the present disclosure.

FIGS. 13A-13E are cross-sectional views of a lower wafer 1300 in a microfluidic bio-entity manipulation and processing system fabricated at various steps according to some embodiments. The lower wafer 1300 in FIGS. 13A-13E may be substantially similar to the lower wafer 1200 in FIGS. 12A-12B. Referring to FIG. 13A, the lower wafer 1300 includes a substrate 1302. The substrate 1302 may include a silicon substrate. In some alternative embodiments, the substrate 1302 may include any other suitable elementary semiconductor, such as diamond or germanium; a suitable compound semiconductor, such as silicon carbide, indium arsenide, or indium phosphide; or a suitable alloy semiconductor, such as silicon germanium carbide, gallium arsenic phosphide, or gallium indium phosphide. The substrate 1302 may be substantially similar to the substrate 502 in FIGS. 5 and 8-9, and/or the substrate 1002 in FIG. 10.

The lower wafer 1300 includes four main functional areas: a fluidic control circuitry area, a solid-state based photosensor array area, a logic circuitry area, and a microfluidic channel area. The circuitry and photosensor array areas are formed in the substrate 1302 and/or in an inter-metal dielectric (IMD) layer 1304 formed on the substrate 1302. The IMD layer 1304 may be formed using any suitable deposition method, such as CVD, PVD, or ALD. The IMD layer 1304 may also be formed using a spin-coating process.

Still referring to FIG. 13A, the fluidic control circuitry area includes fluidic control circuitry 1306, which includes a plurality of metallization layer connected with associated transistors and other circuit components. The sensor array area includes a photosensor array 1308 and photosensor control circuitry 1310. The photosensor array 1308 may be an array of transistor-based photosensors and is a CMOS image sensor array. However, in other embodiments the photosensor array may include photodiodes, active pixel sensors, phototransistors, photoresistors, charged coupled devices, or the like. The photosensor array 1308 is controlled by the photosensor control circuitry 1310, which also includes a plurality of transistors and other circuit components. Finally, in the logic circuitry area, there is a significant amount of logic circuitry 1312 including transistors and other circuit components. The logic circuitry 1312 allows for input to and output from the lower wafer 1302. Further logic circuitry 1312 is coupled to both the photosensor control circuitry 1310 and the fluidic control circuitry 1306, to provide both with signal processing for optimal operation, such as analog-to-digital and digital-to-analog conversion. Fluidic control circuitry 1306, photosensor control circuitry 1310, and logic circuitry 1312 are embedded in the IMD layer 1304. In some embodiments, the lower portion 1202 of the lower wafer 1200 in FIGS. 12A-12B may be substantially similar to the wafer 1302, the fluidic control circuitry area, the sensor array area, and the logic circuitry area in the lower wafer 1300 in FIGS. 13A-13E. The IMD layer 1304, the fluidic control circuitry area, the solid-state based photosensor array area, and the logic circuitry area may be substantially similar to the corresponding components as discussed in FIGS. 5 and 8-10.

As shown in FIG. 13A, a metal layer 1320 is formed on the IMD layer 1304. The metal layer 1320 may include aluminum copper alloy (AlCu) or copper (Cu). The metal layer 1320 may also include any other suitable materials that can be used for the electrodes of the microfluidic bio-entity manipulation and processing system. The metal layer 1320 may be deposited using a sputtering process or an electroplating process. One or more other suitable deposition processes, such as CVD, or ALD may also be used for forming the metal layer 1320. The thickness of the metal layer 1320 is in a range from about 2 µm to about 100 µm.

Figure 13B:
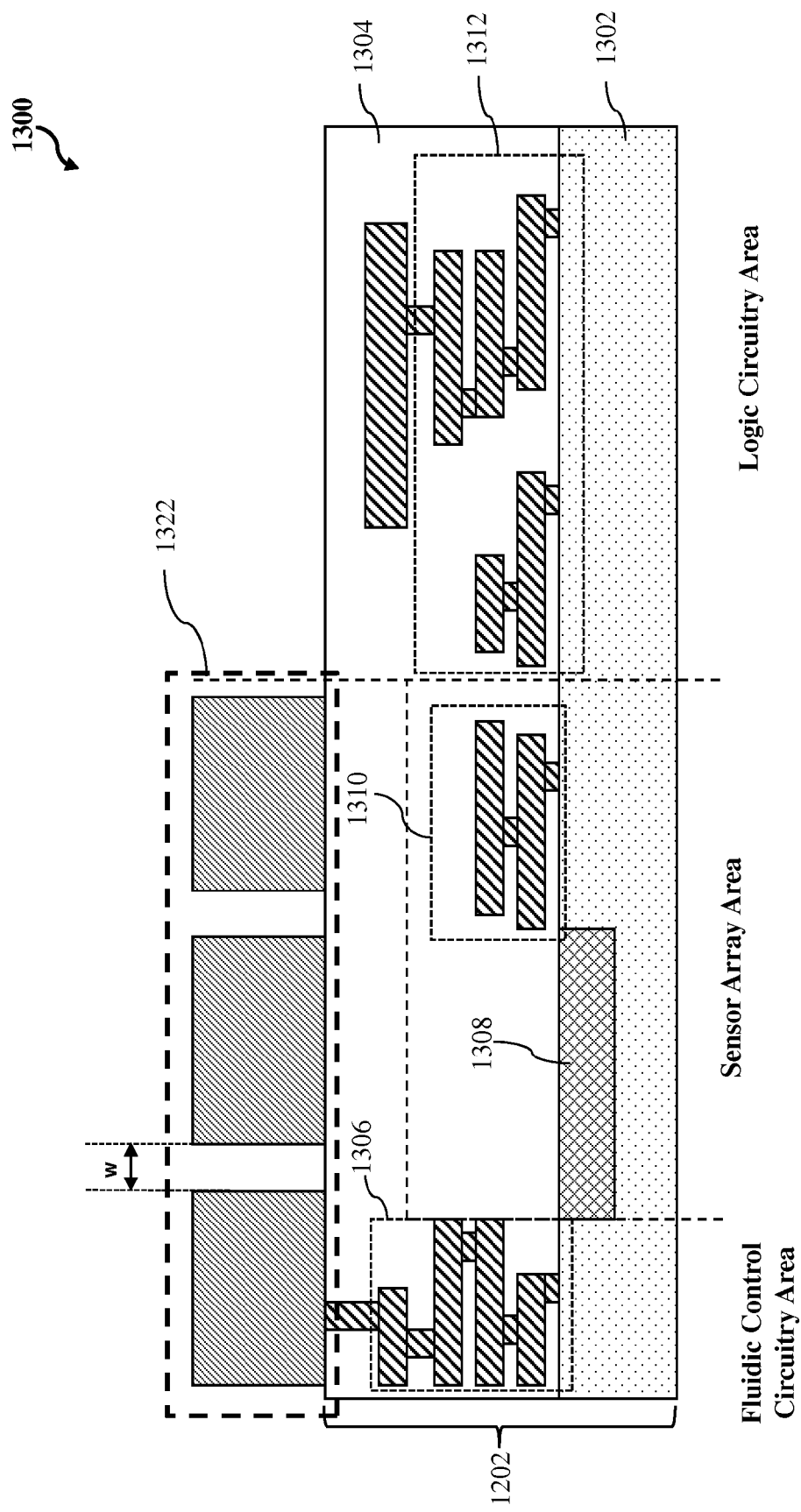

Referring to FIG. 13B, one or more vertical electrodes 1322 are formed in the metal layer 1320 using a lithography process and an etching process. The lithography process may include forming a photoresist layer (resist) overlying the metal layer 1320, exposing the resist to a pattern, performing a post-exposure bake process, and developing the resist to form masking elements including the resist. The masking elements may be used in the lithography process for patterning the metal layer 1320 to define the dimension and the layout of the vertical electrodes 1322. The metal layer 1320 may then be recessed using the masking elements by any appropriate dry etching and/or wet etching methods. The recessing process may include a dry etching process, a wet etching process, or combinations thereof. For example, the metal layer 1320 may be etched using a reactive-ion etching (RIE) process. The masking elements may then be removed from the vertical electrodes 1322 using a suitable etching process, such as a wet stripping process, a plasma ashing process, or any other suitable methods. In some embodiments, the vertical electrodes 1322 may be formed using a lift-off process.

In some embodiments, a damascene process may be used to form the one or more vertical electrodes 1322. For example, during a damascene process, trenches and/or vias are formed in a dielectric material layer, copper or tungsten is then filled in the trenches and/or vias. A chemical mechanical polishing (CMP) process is applied to remove excessive metal on the dielectric material layer and to planarize the top surface.

As shown in FIG. 13B, in some embodiments, the width of the distance (w) between two adjacent vertical electrodes or the width (w) of the microfluidic channel is in a range from about 30 µm to about 1000 µm. The vertical electrodes 1322 in FIGS. 13B-13E may be substantially similar to the vertical electrodes 1210 in FIGS. 12A-12B.

It is to be understood that the three depicted vertical electrodes are exemplary, any number of vertical electrodes may be included in the microfluidic bio-entity manipulation and processing system. In some embodiments, one or more vertical electrodes are in communication with the fluidic control circuitry 1306, and thus may be in an ON or OFF state as described in connection with FIG. 3.

Figure 13C:
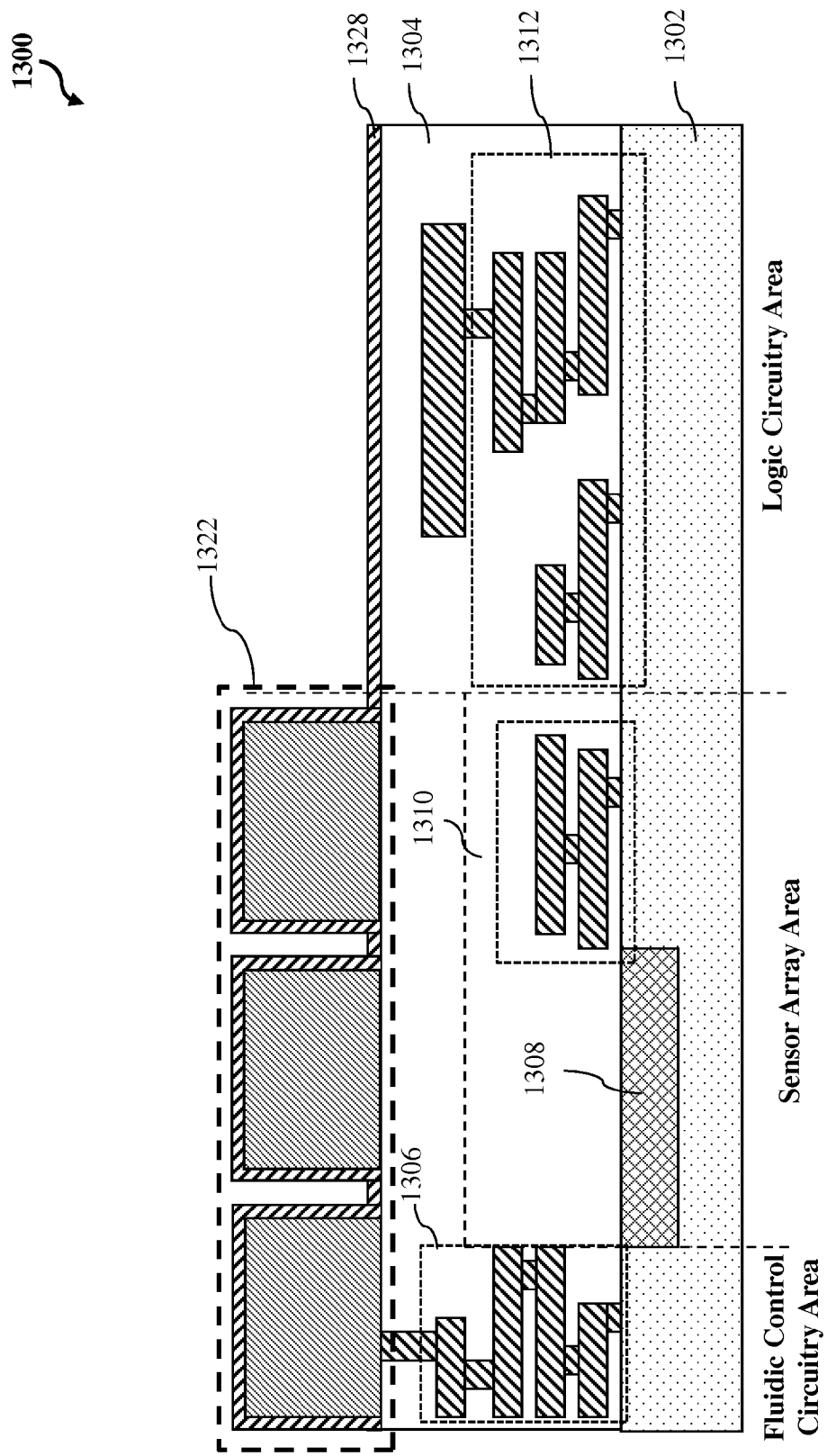

Referring to FIG. 13C, a dielectric layer 1328 is deposited on the one or more vertical electrodes 1322. As shown in FIG. 13C, the dielectric layer 1328 is formed to conform to the surface of the vertical electrodes 1322. In some embodiments, the dielectric layer 1328 is a high-k dielectric layer formed by an atomic layer deposition (ALD) process, or a chemical vapor deposition (CVD) process, then followed by an annealing process. The dielectric layer 1328 includes one or more materials selected from the group consisting of silicon oxide, silicon nitride, aluminum oxide, tantalum oxide, hafnium oxide, and barium strontium titanate. In some examples, the dielectric layer 1328 includes one or more materials selected from the group consisting of $SiO_2$, $Si_3N_4$, $Al_2O_3$, $Ta_2O_5$, $HfO$, and $(Ba, Sr)TiO_3$. In some embodiments, the dielectric constant of the materials in the dielectric layer 1328 is in a range from about 4 to about 800. The thickness of the dielectric layer 1328 is in a range from about 100 Å to about 1 µm. The dielectric layer 1328 in FIGS. 13C-13E may be substantially similar to the dielectric layer 1232 in FIGS. 12A-12B.

Figure 13D:
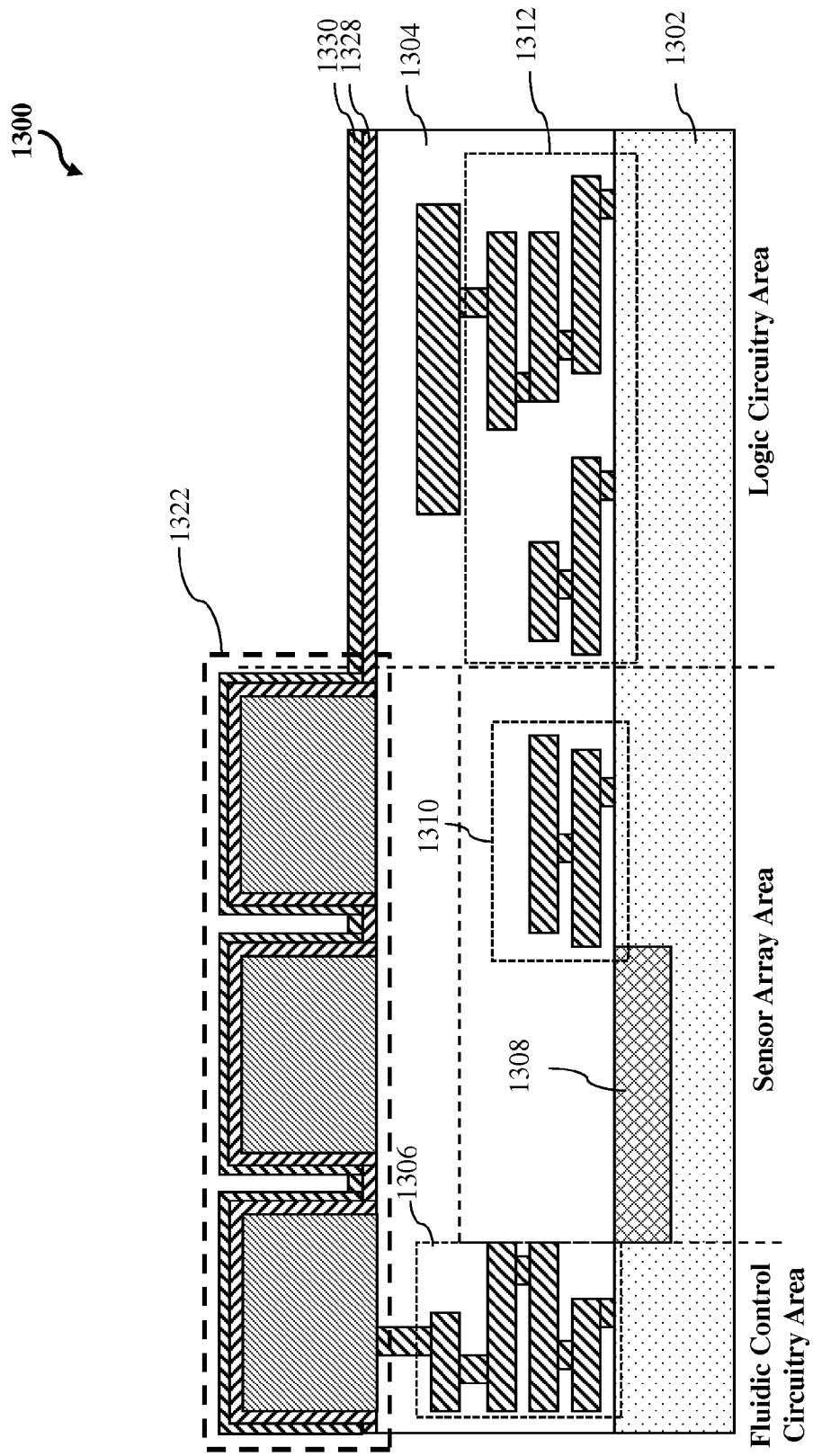

Referring to FIG. 13D, a hydrophobic coating 1330 is formed on the dielectric layer 1328. The hydrophobic coating 1330 is also formed to conform to the surface of the vertical electrodes 1322 and the dielectric layer 1232. In some embodiments, the hydrophobic coating 1330 is made from polytetrafluoroethylene (PTFE), while in other embodiments it is a self-assembled monolayer. The hydrophobic coating 1330 may be formed using a spin-coating process or any other suitable methods. The thickness of the hydrophobic coating 1330 is in a range from about 10 Å to about 1 µm. The hydrophobic coating 1330 in FIGS. 13D-13E may be substantially similar to the dielectric layer 1234 in FIGS. 12A-12B.

Figure 13E:
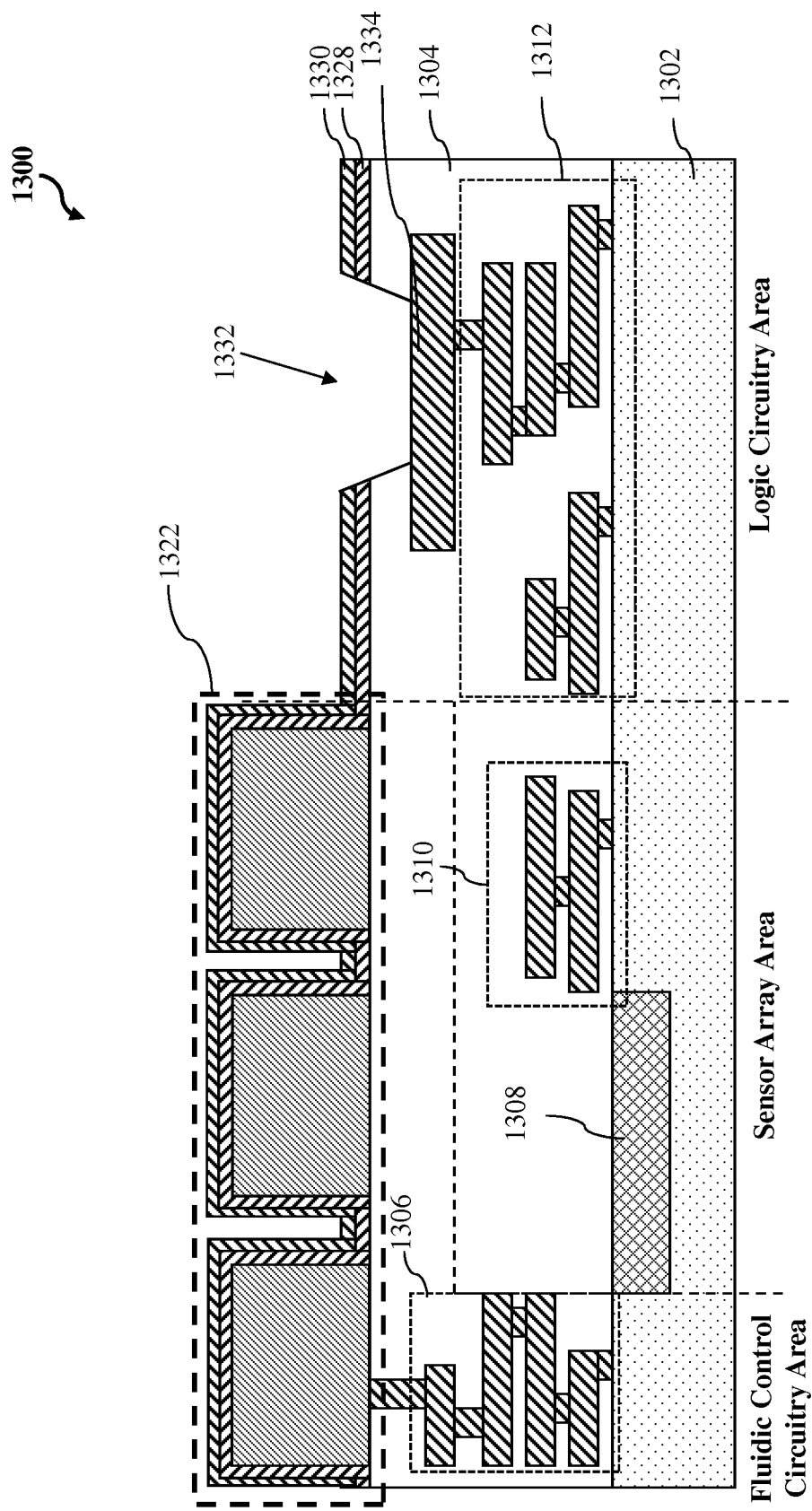

Referring to FIG. 13E, a trench 1332 is formed using a suitable etching process to reveal a contact pad 1334. The trench 1332 may be formed by etching through a portion of the hydrophobic coating 1330, a portion of the dielectric layer 1328, and a thickness of the IMD 1304 to expose an upper surface of the contact pad 1334. The contact pad 1334 may be provided to allow power or ground to be supplied to the lower wafer 1300, or to allow for signal/control input or output. The contact pad 1334 and the process of forming thereof in FIG. 13E may be substantially similar to that of FIG. 5.

Figure 14:
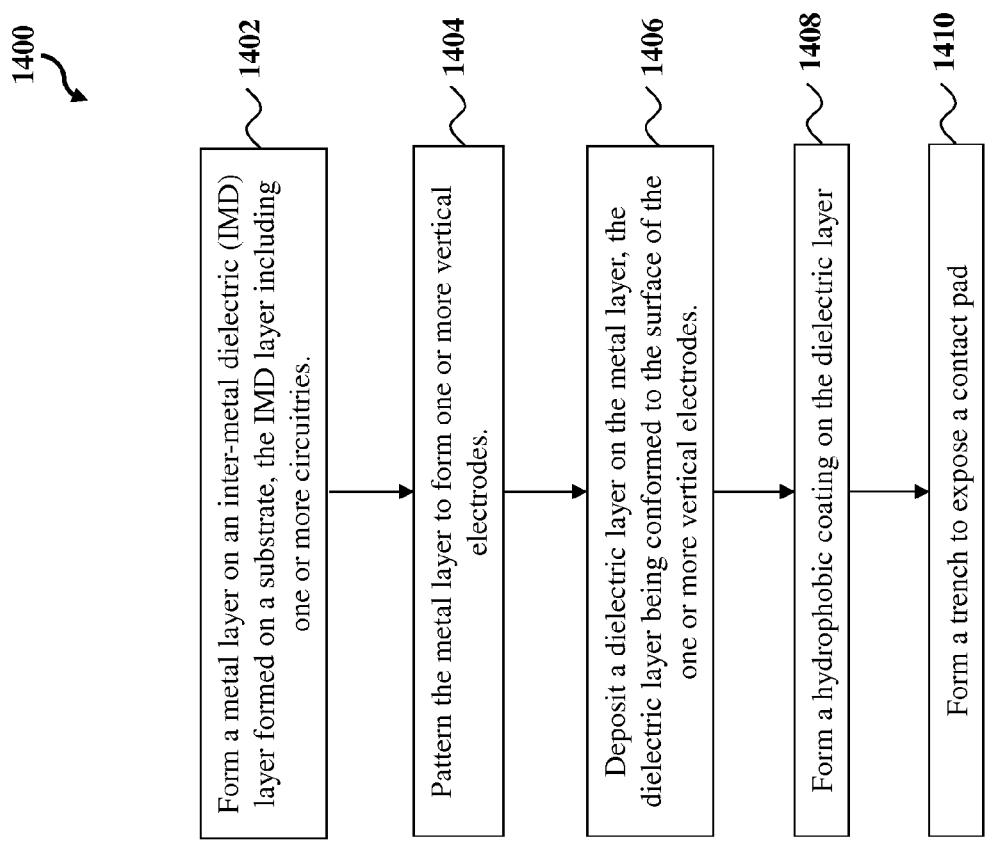
FIG. 14 is a flowchart of a method for forming vertical electrodes in a microfluidic bio-entity manipulation and processing system according to some embodiments of the present disclosure.

FIG. 14 is a flowchart of a method 1400 for forming vertical electrodes 1322 in a microfluidic bio-entity manipulation and processing system according to some embodiments of the present disclosure. It should be understood that additional processes may be provided before, during, and after the method 1400 of FIG. 14, and that some other processes may be briefly described herein. To better illustrate method 1400 in operation, reference will be made to the lower wafer 1300 as discussed in FIGS. 13A-13E. It is to be understood that reference to FIGS. 13A-13E are not supposed to be limiting, and the method 1400 may also be explained with reference to other embodiments of the microfluidic bio-entity manipulation and processing systems in the present disclosure.

Method 1400 starts from a process 1402 by forming a metal layer 1320 on an inter-metal (IMD) layer 1304. The IMD layer 1304 is formed on the substrate 1302, and the IMD layer 1304 includes one or more circuitries. The metal layer 1320, the IMD layer 1304 and the substrate 1302 are provided a lower wafer, e.g., the lower wafer 1300. The lower wafer may include one or more functional areas, such as a fluidic control circuitry area, a solid-state based photosensor array area, a logic circuitry area, and a microfluidic channel area as shown in FIGS. 13A-13E. The circuitry and photosensor array areas may be formed in the substrate 1302 and/or in the inter-metal dielectric layer (IMD) 1304.

Method 1400 proceeds to a process 1404 by patterning the metal layer (e.g., the metal layer 1320) to form one or more vertical electrodes (e.g., the vertical electrodes 1322). The one or more vertical electrodes may be formed using a lithography process and an etching process. One or more masking elements may be used in the lithography process for patterning the metal layer to define the dimension and the layout of the vertical electrodes. The metal layer may then be recessed using the masking elements by any appropriate dry etching and/or wet etching methods, e.g., a RIE process, or a lift-off process. In some alternative embodiments, the one or more vertical electrodes may be formed using a damascene process.

Method 1400 proceeds to a process 1406 by depositing a dielectric layer (e.g., the dielectric layer 1328) on the one or more vertical electrodes 1322. As shown in FIG. 13C, the dielectric layer 1328 is formed to conform to the surface of the vertical electrodes 1322. In some embodiments, the dielectric layer 1328 is a high-k dielectric layer formed by an atomic layer deposition (ALD) process, or a chemical vapor deposition (CVD) process, then followed by an annealing process.

Method 1400 proceeds to a process 1408 by forming a hydrophobic coating (e.g., the hydrophobic coating 1330) on the dielectric layer. The hydrophobic coating 1330 may be formed using a spin-coating process or any other suitable methods.

Method 1400 proceeds to a process 1410 by forming a trench (e.g., the trench 1332) to expose a contact pad (e.g., the contact pad 1334). The trench may be formed using a suitable etching process to reveal the contact pad. The trench 1332 may be formed by etching through a portion of the hydrophobic coating 1330, a portion of the dielectric layer 1328, and a thickness of the IMD 1304 to expose an upper surface of the contact pad 1334 as shown in FIG. 13E.

As disclosed with reference to FIGS. 13A-13E and 14, a patterning process including a lithography process and an etching process may be used to define and form the one or more vertical electrodes on the substrate. The lithography process may be used to define the microfluidic channel formed between two vertical electrodes. The present disclosure may provide improved control and more flexibility in tuning the widths of the channel gaps. For example, the microfluidic channels with various widths of channel gaps as shown in FIG. 12C may be formed using the patterning process as disclosed in the present disclosure.

Figure 15A:
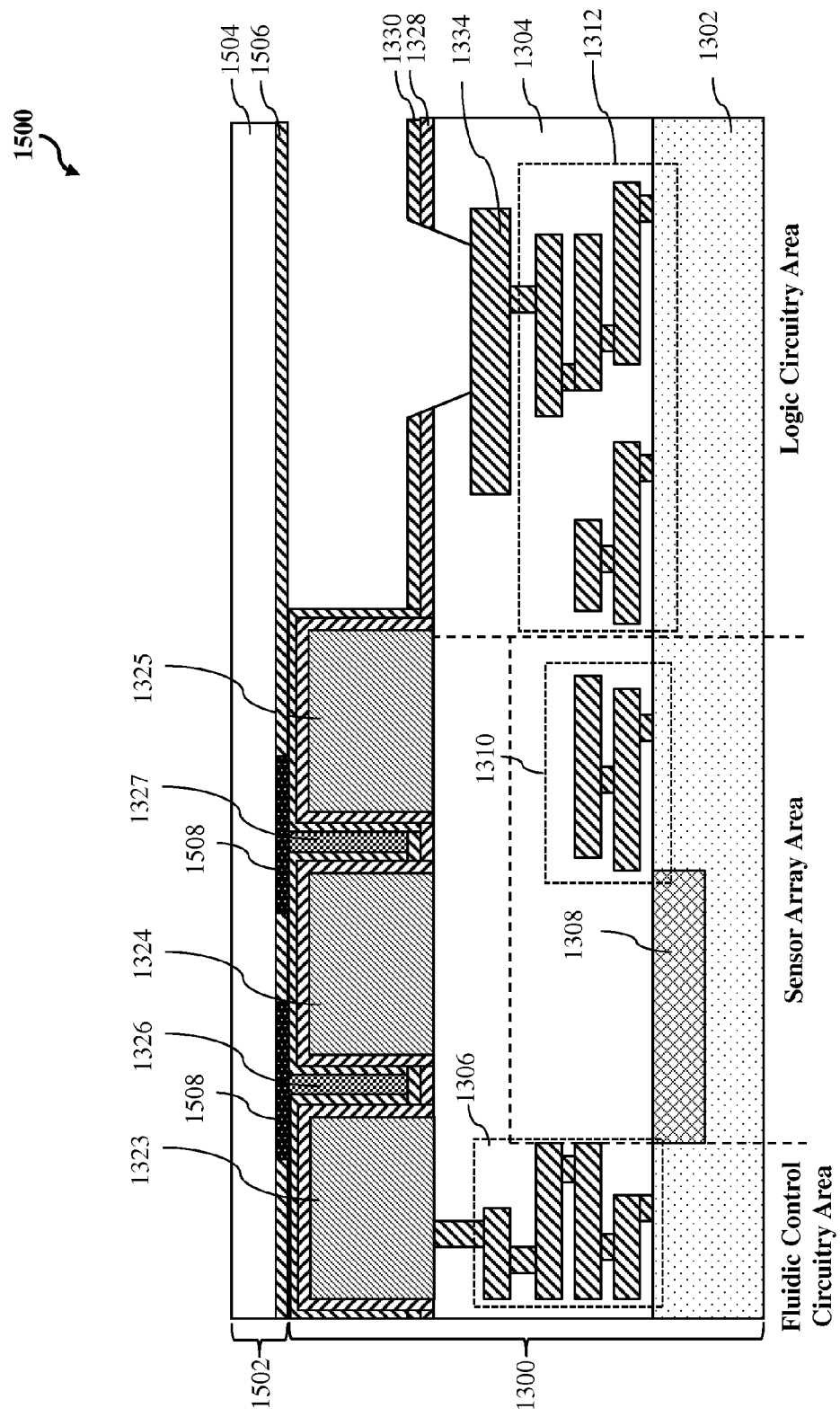
FIG. 15A is a cross-sectional diagram of a microfluidic bio-entity manipulation and processing system according to some embodiments of the present disclosure.

FIG. 15A is a cross-sectional diagram of a microfluidic bio-entity manipulation and processing system 1500 according to some embodiments of the present disclosure. As shown in FIG. 15A, the microfluidic bio-entity manipulation and processing system 1500 includes a lower wafer 1300 as fabricated in FIGS. 13A-13E, and an upper wafer 1502. The microfluidic bio-entity manipulation and processing system 1500 may include the vertical electrodes in the present disclosure for transporting and mixing target bio-entities as discussed with reference to FIG. 4. Actions like those described in connection with FIG. 3 may be used to move, split, merge, and form droplets.

Figure 15B:
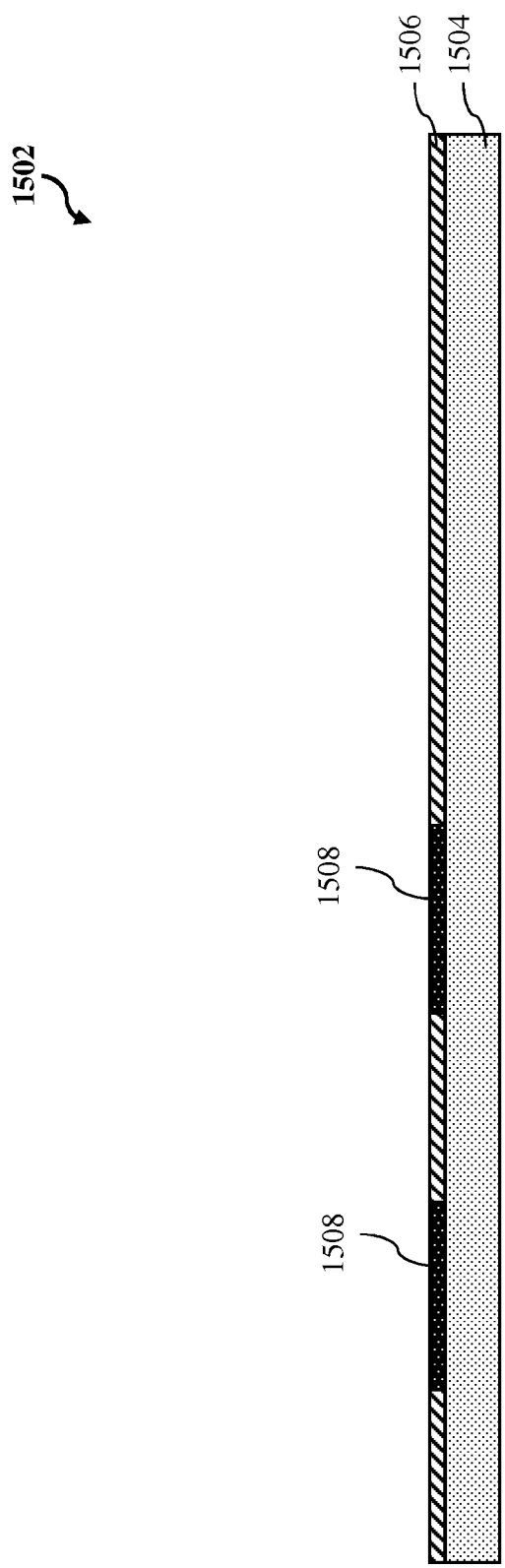
FIG. 15B is a cross-sectional diagram of an upper wafer that may be used in a bio-entity manipulation and processing system according to some embodiments of the present disclosure.

FIG. 15B is a cross-sectional diagram of an upper wafer 1502 that may be used in a bio-entity manipulation and processing system 1500. As shown in FIG. 15B, the upper wafer 1502 may include a substrate 1504 and a hydrophobic coating 1506 formed on the substrate. One or more labeling areas 1508 may be formed in the hydrophobic coating 1506.

Referring back to FIG. 15A, in some embodiments, the upper wafer 1502 may be in direct contact with the one or more vertical electrodes 1322 of the lower wafer 1300. In some alternative embodiments, the upper wafer 1502 may not be in direct contact with the lower wafer 1300. In the present embodiments, a voltage may not be needed to apply to the upper 1502. The electric fields may be applied onto various vertical electrodes in the lower wafer to manipulate the transporting process of the microfluidic droplets.

A bio-entity droplet (e.g., bio-entity droplet 1326 and/or bio-entity droplet 1327) including DNA, antibody and/or protein may be filled in the microfluidic channel formed between adjacent vertical electrodes on the lower wafer 1300. The bio-entity droplet may be brought into contact with the labeling areas 1508 on the upper wafer 1502 for a chemical reaction generating photonic emission. In some embodiments, the colorimetric analysis (e.g., colorimetric determination of glucose), or fluorescent reaction may be implemented into the microfluidic bio-entity manipulation and processing system 1500. The bio-entity droplet may be labeled on bead (e.g., made by gold, polystyrene, magnetic beads which may be controlled by the droplet/microfluidic circuitry.)

For example, referring again to FIG. 4, during the sample preparation, some bio-entity (DNA, antibody, protein) is labeled on the bead (e.g., made by gold, polystyrene, magnetic bead). Afterward, the sample beads could be loaded on the sample tank 410A-410D. By utilizing the droplet/microfluidic circuitry, the bio-sample beads could be carried by the droplet movement from the sample tank and mixed with the reagent to perform the bio-reaction. Then, the photosensors could detect the reaction. In this example, the "sample preparation" is another step before loading fluidic on to the chip.

The contact between the labeling area 1508 and the bio-entity sample droplet 1326 may undergo a chemical reaction which intensifies or enhances the fluorescent light signal. This light passes to the photosensor array 1308 to be detected and a corresponding signal is sent to the logic circuitry 1312 for processing. Logic circuitry 1312 may interpret the signal by color or frequency to determine the biochemical reaction that occurred. The biochemical reaction may indicate that a specific base nucleotide was detected in a target DNA fragment, or that a particular antibody was present in the bio-entity sample droplet. After the bio-entity sample droplet 1326 has been processed, it may be removed from the microfluidic channel.

Figure 16:
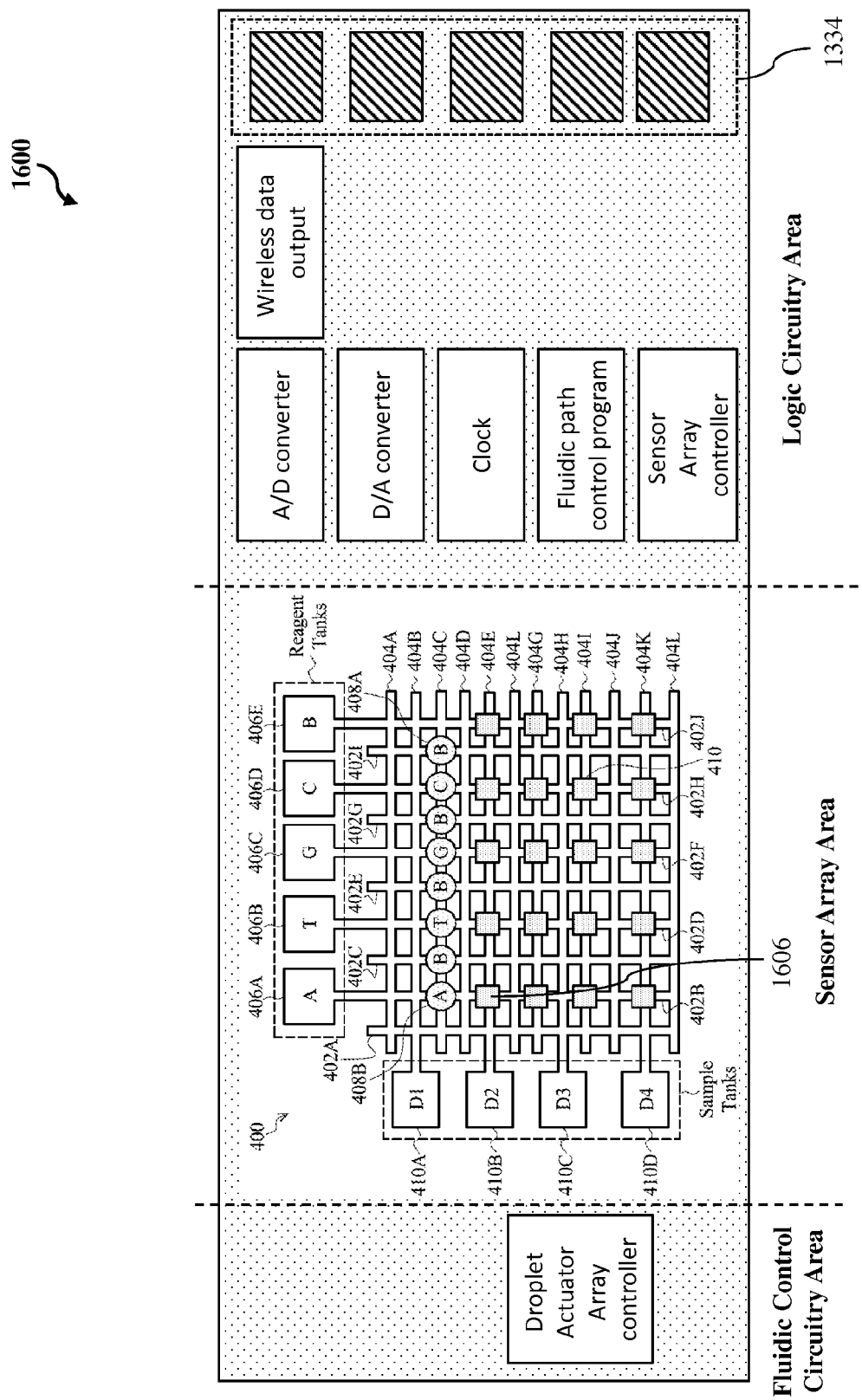
FIG. 16 is an illustrative top view of an integrated device including a microfluidic bio-entity manipulation and processing system according to some embodiments of the present disclosure.

In some examples, the droplet 1326 may include a tagged bio-entity sample, such as DNA mixed with a reagent droplet such as the exemplary adenine reagent droplet 408B from FIG. 4 or FIG. 16. When the droplet 1326 contacts the labeling area 1508, chemical reactions may remove the tag from the bio-entity samples in the droplet 1326. The removal of the tag may enhance or intensify a photonic emission. The photonic emission may be sensed by the photosensor array 1308. This signal is captured by the photosensor control circuitry 1310, and transmitted to the logic circuitry 1312 for signal processing. Depending on the frequency or color of the photonic emission, a specific base pair may be detected.

In some other examples, antibodies in the droplet 1327 are being tested. When the droplet 1327 contacts the labeling area 1508 of the upper wafer 1502, reactions between the droplet 1327 and the labeling area 1508 may result in a photonic emission, which indicates the presence of the particular antibody in the bio-entity sample in droplet 1327.

FIG. 16 is an illustrative top view of an integrated microfluidic bio-entity manipulation and processing device 1600 according to some embodiments of the present disclosure. For the clarity of the discussion, FIG. 16 is discussed as below in reference with FIG. 15A. However, this should not be understood as limiting such features. In some embodiments, one or more of the vertical paths 402A-J and each of horizontal paths 404A-L of the microfluidic grid 400 may be formed from the one or more microfluidic channels formed among a plurality of vertical electrodes as discussed in FIGS. 12A-12C, and fabricated using the processes as discussed in FIGS. 13A-13E and 14.

Referring to FIG. 16, the logic circuitry area may include one or more circuitries for the sensor array controller, fluidic path control program, clock, D/A converter, A/D converter, and the wireless data output. The device 1600 also includes the contact pad 1334 for providing power supply, and/or signal input/output.

Referring to FIG. 16, a sensor array area of the device 1600 includes a microfluidic grid 400 which may be substantially similar to the microfluidic grid 400 as discussed in FIG. 4. The microfluidic grid 400 includes one or more reagent tanks for storing reagents, and one or more samples tanks for storing the bio-entity samples. The reagents may be mixed with the sample droplets for tagging the droplets before the droplets are brought in contact with the labeling areas 1508 of the upper wafer. As shown in FIG. 16, each of the square areas 410 may represent a target DNA fragment, such as exemplary target DNA fragment 410, that can be manipulated as described above in connection with FIG. 3 for various operations, such as the lateral movement 300A, the droplet split 300B, the droplet merger 300C, and the droplet formation 300D. The area underneath the microfluidic grid 400 includes an image sensor array, which may be used to detect photonic signals and to take light-based measurements in order to sequence the target DNA fragment samples. The image sensor array may utilize a front-side illumination or a back-side illumination according to various embodiments of the present disclosure.

Still referring to FIG. 16, the fluidic control circuitry area may include a droplet actuator array controller configured to manipulate the transporting and mixing of each sample droplet. Each vertical electrode as represented by the vertical and horizontal path of the microfluidic grid 400 may be connected to the fluidic control circuitry.

Referring to FIGS. 15A and 16, the bio-entity sample droplet 1326 is moved in the microfluidic channel formed between vertical electrodes using the electrowetting effect. As discussed in FIG. 12A, by controlling the electrical fields, the droplet may be guided into mixing with the reagent from the reagent tanks to be tagged before contacting the labeling area 1508. The droplet in the microfluidic channel may also be guided into contact with the labeling area 1508. For example, a sample droplet provided by sample tank 410B may be transported to contact with a reagent droplet provided by reagent tank 406A at the square 1606, the mixed sample droplet is then brought into contact with the labeling area 1508 for a chemical reaction to generate a photonic signal to be detected by the image sensor array 1308. Guiding the bio-entity sample droplet into contact with the labeling area 1508 may be accomplished by having the logic circuitry 1312 exert control over the fluidic control circuitry 1306.

In some alternative embodiments, the photonic signals detected by the image sensor may be generated by reactions between the bio-entity samples provided by the sample tanks and the reagents provided by the reagent tanks in the microfluidic grid 400. For example, a sample droplet provided by sample tank 410B may be transported to react with a reagent droplet provided by reagent tank 406A at the square 1606, and a photonic signal may be generated by the reaction and may be detected by the image sensor. In addition, one could add the bead with sample approach in this embodiment.

Figure 17:
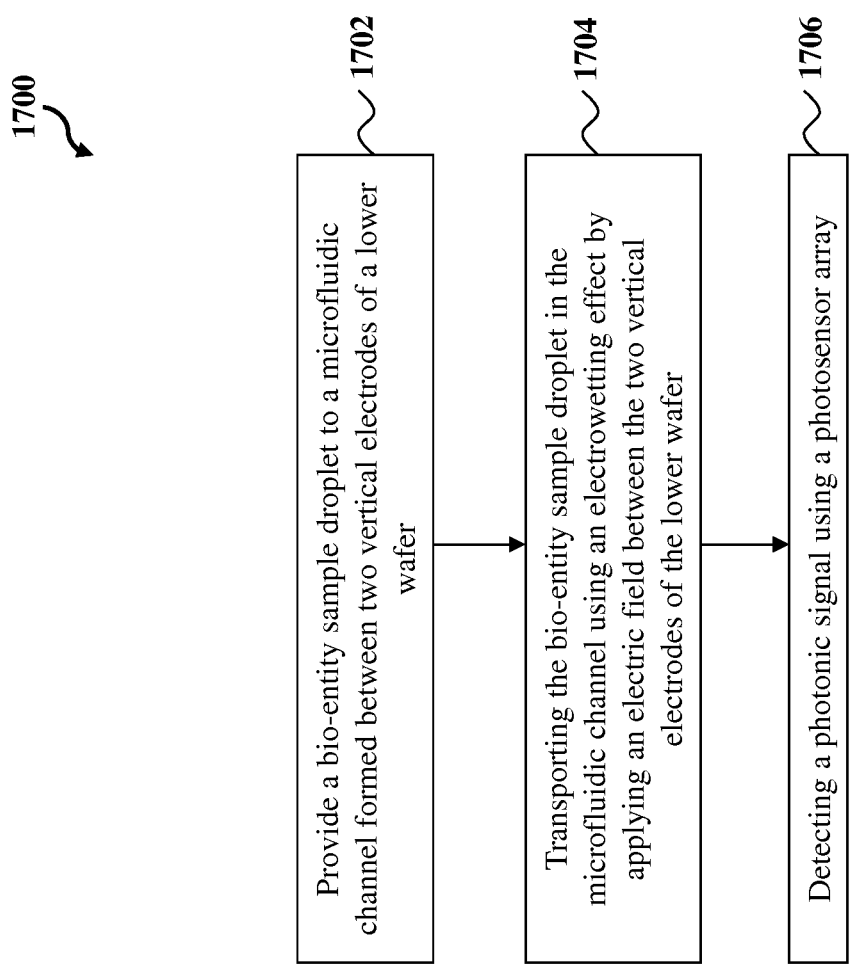
FIG. 17 is a flowchart of a method for manipulating and processing bio-entity samples with a microfluidic bio-entity manipulation and processing system according to some embodiments of the present disclosure.

FIG. 17 is a flowchart of a method 1700 for manipulating and processing bio-entity samples with a microfluidic bio-entity manipulation and processing system according to some embodiments of the present disclosure. The method 1700 begins in step 1702 by providing a bio-entity sample droplet to a microfluidic channel. The bio-entity sample droplet may be obtained from one or more tanks coupled to a microfluidic grid. In some examples, the method 1700 may also include mixing a bio-entity sample from a sample tank with a reagent from a reagent tank of the microfluidic grid 400 to form a bio-entity sample for testing. In an exemplary embodiment of the present disclosure as shown in FIG. 15A, the microfluidic channel is formed between two vertical electrodes on the lower wafer 1300.

The method 1700 proceeds to step 1704 by transporting the bio-entity sample droplet in the microfluidic channel using an electrowetting effect by applying an electric field between the two vertical electrodes. The microfluidic channel is formed between two vertical electrodes on the lower wafer as discussed in FIGS. 13A-13E and 14. When in the microfluidic channel the bio-entity sample droplet may be brought into contact with a labeling area in the upper wafer. A biochemical reaction is triggered upon contact between the bio-entity sample droplet and the labeling area.

The method 1700 then proceeds to step 1706 by detecting a photonic signal produced by the interaction between the bio-entity sample droplet and the labeling area of the upper wafer. The photonic signal is detected by a photosensor array that is embedded in the lower wafer.

The present embodiments describe structure and method for forming vertical electrodes on a lower wafer of a microfluidic bio-entity manipulation and processing system. A microfluidic channel is formed between two adjacent vertical electrodes on the lower wafer for transporting the bio-entity sample droplet. The photonic signal generated from the interaction between the bio-entity sample droplet and the vertical electrodes may be detected using a photosensor array formed in the lower wafer. The mechanisms of the vertical electrodes may provide precise microfluidic channel gap control and simplified manufacturing process. No external fluidic component, such as a pump, a valve, or a mixer, is necessary for the present disclosure. The mechanisms may also provide a flexible fluidic control, such as an addressable fluidic path and/or a better fluidic resolution. In addition, less amount of the sample droplet or the reagent, e.g., a sample droplet or a drop of reagent at pico liters levels, may be used in the microfluidic bio-entity manipulation and processing system including the vertical electrodes as discussed in the present disclosure. The various embodiments of the microfluidic bio-entity manipulation and processing system in the present disclosure may include integrating transistor based light sensor and/or integrating ion sensitive field-effect transistor (ISFET). The integration capability provided in the present disclosure may include various benefits, such as capable of controlling sensor, microfluidic sample, and reagents using electrical signals; offering low cost of fluidic component; offering CMOS compatible process; and potentials for realizing portable device for lab-on-a-chip (LOC) device.

The present disclosure provides a device for manipulating and processing bio-entity samples comprises a first microfluidic channel formed between a first electrode and a second electrode and on a first substrate, the first microfluidic channel coupled to fluidic control circuitry; and logic circuitry coupled to the fluidic control circuitry and a sensor control circuitry. The first electrode and the second electrode are formed on the first substrate.

The present disclosure provides a method for fabricating a semiconductor device for manipulating and processing microfluidic bio-entity samples comprises forming a metal layer on an inter-metal dielectric (IMD) layer formed on a substrate, one or more circuitries being embedded in the IMD layer; patterning the metal layer to form a first electrode and a second electrode, a first microfluidic channel being formed between the first electrode and the second electrode on the IMD layer; and depositing a dielectric layer on the first electrode and the second electrode. The dielectric layer is conformed to surface of the first electrode and the second electrode.

The present disclosure provides a method for manipulating and processing bio-entity samples with a semiconductor device comprises providing a bio-entity sample droplet to a microfluidic channel formed between a first electrode and a second electrode formed on a substrate; transporting the bio-entity sample droplet in the microfluidic channel using an electrowetting effect by applying an electric field between the first electrode and the second electrode; and detecting a photonic signal using a photosensor array. The photonic signal is generated by an interaction between the bio-entity sample droplet and a labeling area on the upper wafer.

The preceding disclosure is submitted by way of discussion and example. It does not exhaust the full scope and spirit of the disclosure and claims. Such variations and combinations as may be apparent to one of skill in the art are considered to be within the scope and spirit of this disclosure. For instance, throughout the disclosure, DNA sequencing is presented as an example, along with pathogen identification. The scope and spirit of the disclosure extends well beyond the limited context of these examples. Thus, the full extent of the disclosure is limited only by the following claims.

What is claimed is:

1. A device for manipulating and processing bio-entity samples, the device comprising:
   a first microfluidic channel formed between a first electrode and a second electrode and on a first substrate, the first microfluidic channel coupled to fluidic control circuitry; and
   logic circuitry coupled to the fluidic control circuitry and a sensor control circuitry,
   wherein the first electrode and the second electrode are formed on the first substrate.

2. The device of claim 1, further comprising:
   a microfluidic grid formed on the first substrate and including the first electrode, the second electrode, and the first microfluidic channel; and
   a photosensor array coupled to the sensor control circuitry,
   wherein the microfluidic grid is coupled to a first reservoir and a second reservoir,
   wherein the microfluidic grid is configured to transport a bio-entity sample by electrowetting, and to mix the bio-entity sample from the first reservoir with a reagent from a second reservoir, and
   wherein the photosensor array is configured to detect a photonic signal.

3. The device of claim 1, wherein the fluidic control circuitry, the sensor control circuitry, and the logic circuitry are embedded in an inter-metal dielectric (IMD) layer formed on the first substrate, and
   wherein the first electrode and the second electrode are formed on the IMD layer.

4. The device of claim 1, further comprising:
   a dielectric layer formed on each of the first electrode and the second electrode, the dielectric layer being conformed to surface of each of the first electrode and the second electrode; and
   a hydrophobic coating formed on the dielectric layer.

5. The device of claim 4, wherein the dielectric layer includes one or more materials selected from the group consisting of SiO2, Si3N4, Al2O3, Ta2O5, HfO, and (Ba, Sr)TiO3.

6. The device of claim 4, wherein a thickness of the dielectric layer is in a range from about 100 Å to about 1 μm.

7. The device of claim 4, wherein a thickness of the hydrophobic coating is in a range from about 10 Å to about 1 μm.

8. The device of claim 4, further comprising a labeling area configured to interact with the bio-entity sample to generate a photonic signal to be detected by a photosensor array coupled to the sensor control circuitry.

9. The device of claim 1, wherein a width of the first microfluidic channel is in a range from about 30 μm to about 1000 μm.

10. The device of claim 1, further comprising:
    a second microfluidic channel formed between a third electrode and a fourth electrode,
    wherein the second microfluidic channel, the third electrode, and the fourth electrode are formed on the first substrate, and
    wherein a width of the first microfluidic channel is different from a width of the second microfluidic channel.

11. The device of claim 1, wherein a height of each of the first electrode and the second electrode is in a range from about 2 μm to about 100 μm.

12. The device of claim 1, wherein a length of each of the first electrode and the second electrode is in a range from about 50 μm to about 1000 μm.

13. A method for fabricating a semiconductor device for manipulating and processing microfluidic bio-entity samples, the method comprising:
    forming a metal layer on an inter-metal dielectric (IMD) layer formed on a substrate, one or more circuitries being embedded in the IMD layer;
    patterning the metal layer to form a first electrode and a second electrode, a first microfluidic channel being formed between the first electrode and the second electrode on the IMD layer; and
    depositing a dielectric layer on the first electrode and the second electrode, the dielectric layer being conformed to surface of the first electrode and the second electrode.

14. The method of claim 13, further comprising:
    forming a hydrophobic coating on the dielectric layer.

15. The method of claim 13, wherein the patterning the metal layer includes:
    performing a lithography process to the metal layer to form one or more masking elements; and
    etching the metal layer using the one or more masking elements to form the first electrode and the second electrode on the IMD layer.

16. The method of claim 15, wherein the etching the metal layer further comprises:
    etching the metal layer to form a third electrode and a fourth electrode on the IMD layer,
    wherein a second microfluidic channel is formed between the third electrode and the fourth electrode, and
    wherein a width of the first microfluidic channel is different from a width of the second microfluidic channel.

17. The method of claim 13, wherein depositing the dielectric layer includes depositing the dielectric layer on and conformed to the surface of the first electrode and the second electrode using one or more methods selected from the group consisting of an atomic layer deposition (ALD) process and a chemical vapor deposition (CVD) process.

18. The method of claim 13, further comprising:
forming a trench to expose a contact pad embedded in the IMD layer.

19. A method for manipulating and processing bio-entity samples with a semiconductor device, the method comprising:
providing a bio-entity sample droplet to a microfluidic channel formed between a first electrode and a second electrode formed on a substrate;
transporting the bio-entity sample droplet in the microfluidic channel using an electrowetting effect by applying an electric field between the first electrode and the second electrode; and
detecting a photonic signal using a photosensor array, wherein the photonic signal is generated by an interaction between the bio-entity sample droplet and a labeling area.

20. The method of claim 19, further comprising:
mixing the bio-entity sample droplet with a reagent droplet,
wherein the photonic signal is generated by a reaction between the bio-entity sample droplet and the reagent droplet.

* * * * *